(12) United States Patent
Tigli et al.

(10) Patent No.: US 8,018,010 B2
(45) Date of Patent: Sep. 13, 2011

(54) CIRCULAR SURFACE ACOUSTIC WAVE (SAW) DEVICES, PROCESSES FOR MAKING THEM, AND METHODS OF USE

(75) Inventors: Onur Tigli, Vancouver, WA (US); Mona Zaghloul, Bethesda, MD (US)

(73) Assignee: The George Washington University, Washington, DC (US)

(*) Notice: Subject to any disclaimer, the term of this patent is extended or adjusted under 35 U.S.C. 154(b) by 253 days.

(21) Appl. No.: 12/166,646

(22) Filed: Jul. 2, 2008

(65) Prior Publication Data
US 2009/0114798 A1    May 7, 2009

Related U.S. Application Data

(63) Continuation-in-part of application No. 11/738,460, filed on Apr. 20, 2007.

(51) Int. Cl.
*H01L 29/68* (2006.01)
(52) U.S. Cl. .................. 257/416; 257/E45.006
(58) Field of Classification Search .................. 257/416, 257/E45.006; 250/200; 310/313 R; 331/167
See application file for complete search history.

(56) References Cited

U.S. PATENT DOCUMENTS

| | | | |
|---|---|---|---|
| 4,065,735 A | 12/1977 | Palfreeman et al. | |
| 4,065,736 A | 12/1977 | London | |
| 4,124,828 A | 11/1978 | Bert | |
| 4,194,171 A | 3/1980 | Jelks | |
| 4,387,355 A | 6/1983 | Uno et al. | |
| 4,453,242 A * | 6/1984 | Toda | 369/132 |
| 4,665,374 A | 5/1987 | Fathimulla | |
| 5,196,720 A | 3/1993 | Sugai et al. | |
| 5,477,098 A * | 12/1995 | Eguchi et al. | 310/313 R |
| 5,559,483 A | 9/1996 | Kajihara et al. | |
| 5,571,401 A | 11/1996 | Lewis et al. | |
| 6,336,368 B1 | 1/2002 | Chung et al. | |
| 6,448,064 B1 | 9/2002 | Vo-Dinh et al. | |

(Continued)

FOREIGN PATENT DOCUMENTS
WO    2004012331 A1    2/2004

OTHER PUBLICATIONS

U.S. Appl. No. 12/405,503, filed Mar. 17, 2009, George Washington University.

(Continued)

*Primary Examiner* — Allan R Wilson
(74) *Attorney, Agent, or Firm* — Panitch Schwarze Belisario & Nadel LLP

(57) ABSTRACT

The design, fabrication, post-processing and characterization of a novel circular design SAW (Surface Acoustic Wave) based bio/chemical sensor in CMOS technology is introduced. The sensors are designed in AMI 1.5 μm 2 metal, 2 poly process. A unique maskless post processing sequence is designed and completed. The three post-processing steps are fully compatible with any CMOS technology. This allows any signal control/processing circuitry to be easily integrated on the same chip. ZnO is used as the piezoelectric material for the SAW generation. A thorough characterization and patterning optimization of the sputtered ZnO was carried out. The major novelties that are introduced in the SAW delay line features are: The embedded heater elements for temperature control, compensation and acoustic absorbers that are designed to eliminate edge reflections and minimize triple transit interference. Both of these attributes are designed by using the CMOS layers without disturbing the SAW performance.

15 Claims, 13 Drawing Sheets

(a) Layout top view for the novel circular SAW architect completed in Cadence virtuoso layout editor (b) Top view snapshot of the fabricated chip in AMI 0.5 um 3-metal 2-poly technology

U.S. PATENT DOCUMENTS

| | | | |
|---|---|---|---|
| 6,495,892 | B2 | 12/2002 | Goodman et al. |
| 6,580,198 | B2 | 6/2003 | Nakano et al. |
| 6,627,154 | B1 | 9/2003 | Goodman et al. |
| 6,657,269 | B2 | 12/2003 | Migliorato et al. |
| 6,686,675 | B2 | 2/2004 | Koshido |
| 6,743,581 | B1 | 6/2004 | Vo-Dinh |
| 6,842,091 | B2 | 1/2005 | Yip |
| 6,877,209 | B1 | 4/2005 | Miller et al. |
| 6,933,808 | B2 * | 8/2005 | Ma et al. .................. 333/193 |
| 6,937,052 | B2 | 8/2005 | Tam |
| 6,937,114 | B2 | 8/2005 | Furukawa et al. |
| 6,951,047 | B2 | 10/2005 | Tomioka et al. |
| 7,170,213 | B2 * | 1/2007 | Yamanaka et al. ........ 310/313 R |
| 7,400,219 | B2 | 7/2008 | Furuhata et al. |
| 7,473,551 | B2 | 1/2009 | Warthoe |
| 7,498,898 | B2 | 3/2009 | Nakanishi et al. |
| 7,647,814 | B2 * | 1/2010 | Nakaso et al. ............. 73/24.01 |
| 2002/0041218 | A1 * | 4/2002 | Tonegawa et al. .......... 333/133 |
| 2003/0231082 | A1 | 12/2003 | Takata et al. |
| 2004/0021403 | A1 | 2/2004 | Ayazi et al. |
| 2004/0070312 | A1 | 4/2004 | Penunuri et al. |
| 2004/0178698 | A1 | 9/2004 | Shimoe et al. |
| 2004/0189148 | A1 * | 9/2004 | Yamanaka et al. ........ 310/313 R |
| 2004/0232802 | A1 | 11/2004 | Koshido |
| 2004/0245891 | A1 | 12/2004 | Kawachi et al. |
| 2005/0029960 | A1 | 2/2005 | Roh et al. |
| 2005/0131998 | A1 | 6/2005 | Takashima |
| 2005/0242891 | A1 * | 11/2005 | Ash ......................... 331/107 A |
| 2005/0281210 | A1 * | 12/2005 | Makino ........................ 370/275 |
| 2006/0197408 | A1 | 9/2006 | Chen |
| 2006/0230833 | A1 | 10/2006 | Liu et al. |
| 2007/0159027 | A1 * | 7/2007 | Tsai et al. ................. 310/313 R |
| 2009/0114798 | A1 | 5/2009 | Tigli et al. |
| 2010/0029226 | A1 * | 2/2010 | Visser ........................ 455/115.1 |

OTHER PUBLICATIONS

U.S. Appl. No. 11/738,460, filed Apr. 20, 2007, George Washington University.
U.S. Appl. No. 12/166,601, filed Jul. 2, 2008, George Washington University.
Smole et al.; "Magnetically tunable SAW-resonator," Frequency Control Symposium and PDA Exhibition Jointly with the 17th European Frequency and Time Forum, 2003. Proceedings of the 2003 IEEE International , vol., No. pp. 903-906, May 4-8, 2003.
Pohl et al.; "Wireless sensing using oscillator circuits locked to remote high-Q SAW resonators," Ultrasonics, Ferroelectrics and Frequency Control, IEEE Transactions on , vol. 45, No. 5 pp. 1161-1168, Sep. 1998.
Nomura et al.; "Chemical sensor based on surface acoustic wave resonator using Langmuir-Blodgett film", Ultrasonics, Ferroelectrics and Frequency Control, IEEE Transactions on , vol. 45, No. 5 pp. 1261-1265, Sep. 1998.
Datta; "Resonators", Prentice Hall, 1986, ch. 10, pp. 225-239.
Ruby et al.; "Thin film bulk wave acoustic resonators (FBAR) for wireless applications," Ultrasonics Symposium, 2001 IEEE , vol. 1, No. pp. 813-821 vol. 1, 2001.
Visser, "Surface acoustic wave filter in ZnO-SiO2-Si layered structures: Design, technology and monolithic integration with electronic circuitry," Ph.D. dissertation, Delft University of Technology. Delft, the Netherlands, Dec. 1989.
Baca et al.; "Development of a GaAs monolithic surface acoustic wave integrated circuit", IEEE J. Solid-State Circuits, vol. 34. No. 9, Sep. 1999.
Nordin et al.; "Design and Implementation of 1 GHz Resonator Utilizing Surface Acoustic Wave," presented at the Int. Sym. Circuits and Systems, Kos, Greece, 2006.
Morgan "Analysis of Interdigital Transducers," Surface-Wave Devices for Signal Processing, New York: Elesevier Science, 1985, Ch. 4, pp. 57-105.
vanZeijl, "Fundamental aspects and design of an FM upconversion receiver front-end with on-chip SAW filters," Ph. D. dissertation, Delft University of Technology. Delft, Netherlands, Feb. 1990.

Datta et al.; "An analytical theory for the scattering of surface acoustic waves by a single electrode in a periodic array on a piezoelectric substrate", J.Appl.Phys, vol. 51, pp. 4817-4823, 1980.
Tigli et al.; "Design and Fabrication of a Novel SAW Bio/Chemical Sensor in CMOS", in 2005 Proc. IEEE Sensors Conf., pp. 137-140.
Vellekoop; "A Smart Lamb-Wave Sensor System", Ph.D. dissertation, Delft University of Technology. Delft, the Netherlands, Dec. 1989.
Zhu et al.; "Wet-Chemical Etching of (112 ?0) ZnO Films", Journal of Electronic Materials; Jun. 2004, vol. 33, No. 6, pp. 556-559.
IEEE Standard on Piezoelectricity, ANSI/IEEE Standard 176, New York, NY, 1987.
Bingxue; 2001, "Challenges in RF analog integrated circuits", ASIC, IEEE Proceedings. 4th International Conference on, pp. 800-805.
Huang et al.; "The impact of scaling down to deep submicron on CMOS RF circuits," Solid-State Circuits, IEEE Journal of, 1998, 33, (7), pp. 1023-1036.
Steyaert et al.; "Low-voltage low-power CMOS-RF transceiver design," Microwave Theory and Techniques, IEEE Transactions on, 2002, 50, (1), pp. 281-287.
Campbell, "Surface Acoustic Wave Devices for Mobile and Wireless Communications," Academic Press, 1998, pp. 114-122.
Wu et al., "Analysis and Design of Focused Interdigital Transducers," IEEE Transactions on Ultrasonics, Ferroelectrics, and Frequency Control, vol. 52, No. 8, Aug. 2005, pp. 1384-1392.
Qiao et al., "Focusing of Surface Acoustic Wave on a Piezoelectric Crystal," Chin. Phys. Lett, vol. 23, No. 7, 2006, pp. 1834-1837.
Oezguer et al., "A comprehensive review of ZnO materials and devices," Journal of Applied Physics, vol. 98, 2005, pp. 041301-1-041301-103.
Tigli et al., "A Novel Saw Device in CMOS: Design, Modeling, and Fabrication," IEEE Sensors Journal, vol. 7, No. 2, Feb. 2007, pp. 219-227.
Tigli et al., "Design and Fabrication of a novel SAW Bio/Chemical Sensor in CMOS," IEEE Sensors Journal, Oct. 2005, pp. 137-140.
Tigli et al., "Design, Modeling, and Characterization of a Novel Circular Surface Acoustic Wave Device," IEEE Sensors Journal, vol. 8, No. 11, Nov. 2008, pp. 1807-1815.
Tigli et al., "A Novel Circular SAW (Surface Acoustic Wave) Device in CMOS," IEEE Sensors Conference, 2007, pp. 474-477, Oct. 2007.
Buff et al.; "Universal pressure and temperature SAW sensor for wireless applications," Ultrasonics Symposium, 1997. Proceedings., 1997 IEEE , vol. 1, No. pp. 359-362 vol. 1, Oct. 5-8, 1997.
Vellekoop et al.; "Acoustic-wave based monolithic microsensors", Invited, Proc. IEEE Ultrasonics Symposium, Cannes, France, (1994), pp. 565-574.
Morgan, "Surface-Wave Devices for Signal Processing," Studies in Electrical and Electronic Engineering 19, 1985, pp. 129-155.
Farnell, "Elastice Surface Waves," Surface Wave Filters; Design, Construction, and Use, 1977, pp. 1-53.
Standard definitions and methods of measurement for piezoelectric vibrators, ANSI/IEEE Standard 177, New York, NY, May 1966.
Iwai; 2000, "CMOS technology for RF application", Proc. 22nd International Conference on Microelectronics (MIEL ZOOO), vol. 1, NIŠ, Serbia, May 14-17, 2000, 1, pp. 27-34 vol. 21.
Hassan et al.; 2004, "Impact of technology scaling on RF CMOS", IEEE SOC Conference,, pp. 97-101.
Burghartz; 2001, "Tailoring logic CMOS for RF applications", VLSI Technology Systems and Applications, pp. 150-153.
Iwai; 2004, "RF CMOS technology", Radio Science Conference, IEEE Proceedings Asia-Pacific, pp. 296-298.
Lin et al.; 1998, "Micropower CMOS RF components for distributed wireless sensors", Radio Frequency Integrated Circuits (RFIC) Symposium, IEEE, pp. 157-160.
Tan et al., "Minmization of Diffraction Effects in Saw Devices Using a Wide Aperture," Ultrasonics Symposium, 1986, pp. 13-17.
Nakagawa, "A New Saw Convolver Using Multi-Channel Waveguide," Ultrasonics Symposium, 1991, pp. 255-258.
Green et al. "Focused Surface Wave Transducers on Aniosotropic Substrates: A Theory for the Waveguided Storage Correlaor," Ultrasonics Symposium, 1980, pp. 69-73.

Wilcox et al., "Time-Fourier transform by a focusing array of phased surface acoustic wave transducers," J. Appl., Phys. vol. 58, No. 3, Aug. 1985, pp. 1148-1159.

Brooks et al., Saw RF Spectrum Analyzer/Channelizer Using a Focusing, Phased Array Transducer, Ultrasonics Symposium, 1985, pp. 91-95.

Fang et al., "SAW Focusing by Circular-Arc Interdigital Transducers on YZ-LiNbO3," IEEE Transactions on Ultrasonics, Ferroelectrics, and Frequency Control, vol. 36, No. 2, Mar. 1989, pp. 178-184.

Kharusi et al., "On Diffraction and Focusing in Anistropic Crystals," Proceedings of the IEEE, vol. 60, No. 8, Aug. 1972, pp. 945-956.

Coventor, 3D MEMS Design Automation & Virtual Fabrication—Coventor at http:www.coventor.com.

Office Action Issued Mar. 29, 2011 in U.S. Appl. No. 11/738,460.

* cited by examiner

SAW diffraction problem due to finite aperture.

(a) Layout top view for the novel circular SAW architect completed in Cadence virtuoso layout editor (b) Top view snapshot of the fabricated chip in AMI 0.5 um 3-metal 2-poly technology Circular SAW geometry and design paramaters Simulated response for the crossed field based model of the Circular device with angular correction. Conventional rectangular device response is superimposed for comparison. 6 dB insertion loss improvement is observed.

Fig. 5 (a) Meshed circular SAW delay line with input/output IDTs and transparent display of top piezoelectric layer (b) Close-up snapshot of the meshed IDT and the piezoelectric material with fine tetrahedron elements.

Harmonic displacements of circular SAW in frequency domain. The center frequency is found to be 321.8 MHz where the maximum displacement in all directions occur.

Displacement vector distribution of the circular architecture for a transient simulation of 30 ns. The maximum displacement is obtained at the focal point of the output IDT.

Average voltage at the output IDT of the circular architecture. A 30 ns (each simulation step = 1 ns) simulation shows the voltage induced at the output IDT. The maximum voltage is 0.055 V which translates into an insertion loss of - 25.19 dB.

CIRCULAR SURFACE ACOUSTIC WAVE (SAW) DEVICES, PROCESSES FOR MAKING THEM, AND METHODS OF USE

PRIORITY

This application is a continuation-in-part application and claims priority benefit of the earlier filing date under 35 USC 120 of U.S. patent application Ser. No. 11/738,460 filed 20 Apr. 2007, the content of which is incorporated herein in its entirety.

GOVERNMENT INTEREST

This was supported in part by NSF under Grant 0225431.

BACKGROUND

1. Field of the Invention

The present invention relates to the field of surface acoustic wave (SAW) devices, and specifically to improvements to in their design and manufacturing which then provides additional applications for use.

2. Description of the Prior Art

Acoustic wave sensors use a detection arrangement that is based on perturbations to mechanical or acoustic waves. As an acoustic wave propagates through or on the surface of the acoustive wave sensor material, any changes to the physical or chemical characteristics of the wave path may affect the velocity and/or amplitude of the acoustic wave. These changes may be correlated to the corresponding physical, chemical, or biological quantities being measured to provide sensing.

There may be various biological and chemical sensors, using fiber optics, chemical interactions, and various fluorescence approaches. Such sensors may, however, have various weaknesses, such as, for example, low sensitivity, selectivity, or an inability to be hybridized or integrated into sensing chip technology. Acoustic wave (AW) sensors, however, may be better suited for use in biological and chemical detection. As discussed in D. S. Ballantine, R. M. White, S. J. Martin, A. J. Ricco, E. T. Zellers, G. C. Frye, H. Wohltjen, "Acoustic Wave Sensor—Theory, Design, and Physico-Chemical Applications", Academic Press, (1997), acoustic wave sensors may use piezoelectric crystals, which may allow transduction between electrical and acoustic energies. The AW sensor may use piezoelectric material to convert a high frequency signal into an acoustic wave, and the higher frequency may enable the sensor to be more sensitive to surface perturbations.

Piezoelectric materials used for acoustic wave sensors may include quartz ($SiO_2$), lithium niobate ($LiNbO_3$), zinc oxide (ZnO), and others. Each of these materials may possess specific advantages and disadvantages, which may relate to, for example, cost, temperature dependence, attenuation, and propagation velocity. Such materials may, however, have varying transverse acoustic wave velocities, low electromechanical coupling coefficients, non-linear temperature coefficients, and may react chemically with the environment. (See the background information in C. Caliendo, G. Saggio, P. Veradi, E. Verona, "Piezoelectric AlN Film for SAW Device Applications", Proc. IEEE Ultrasonic Symp., 249-252, (1992) and K. Kaya, Y. Kanno, I. Takahashi, Y. Shibata, T. Hirai, "Synthesis of AlN Thin Films on Sapphire Substrates by Chemical Vapor Deposition of $AlCl_3$—$NH_3$ Systems and Surface Acoustic Wave Properties", Jpn. J. Appl. Phys. Vol. 35, 2782-2787, (1996) and G. Carlotti et al., "The Elastic Constants of Sputtered AlN Films", Proc. IEEE Ultrasonic Symp., 353, (1992)).

Previously, creation of SAW devices has been complicated and, in the case of CMOS fabrication, it has been unworkable as the chip would be destroyed by the temperatures required to integrate the SAW device.

One of the major distortions in the transfer characteristics of SAW devices occurs due to the angular spreading of the surface wave. This spreading occurs due to the finite aperture of the conventional SAW IDTs (Interdigital Transducers). The finite aperture causes a curved wavefront rather than the desired flat one which in turn generates increased insertion loss, passband distortion and reduction of out of band rejection [1]. FIG. 1 depicts this phenomenon. The diffraction can be decreased by employing wider acoustic apertures. An improvement of up to 30 dB in out of band rejection was realized by increasing the IDT finger apodization overlap as in [2]. This compensation requires careful adjustment of both the amplitude and phase of the SAW radiated by each IDT finger and is achieved by using IDTs with split-electrode geometries [3].

In the SAW literature, focusing interdigital transducers (FIDT) have been extensively utilized in devices such as convolvers [4], storage correlators [5], time-Fourier transformers [6], and radio frequency (RF) channelizers [7]. All of these devices employed the FIDTs to generate high intensity acoustic fields. The focusing phenomena of SAW fields have also drawn recent interests. Wu et al. [8] gave a detailed account of analysis and design of focused IDTs. In their work, they adopted the exact angular spectrum of plane wave theory (ASoW) to calculate amplitude fields of FIDTs on Y-Z Lithium Niobate ($LiNbO_3$) substrates. Qiao et al. [9] on the other hand, applied rigorous vector field theory of surface excitation on the crysTal to investigate the focusing phenomena. As concluded, the theoretical results demonstrate that anisotropy of the medium has a great impact on the focusing properties of the acoustic beams, such as focal length and symmetrical distributions near the focus [9]. Although FIDTs have been proposed extensively in ultrasonic and acoustic literature for many years, most of them focused on curved IDTs. The most prominent architecture that was investigated in this realm is circular-arc interdigital transducer (CIDT). In their work Fang et al. [10] demonstrated the focusing characteristics of a CIDT on Y-Z Lithium Niobate ($LiNbO_3$) using the angular spectrum theory and experimental velocity data. They concluded that the use of CIDT on Y-Z $LiNbO_3$ can provide a very narrow and long focused acoustic field rather than a localized focal point. They also suggested that CIDT structure does not construct efficient focusing for very highly anisotropic materials. Conventional circular arc structures were also employed in [8] and [9]. Kharusi et al. proposed the FIDT shape as the wave surface [11]. They reported that its focusing ability is better than that of the FIDTs with circular arc shape. The wave surface is the locus of points tracked by the end of the energy velocity vector which is drawn from a fixed original point. The idea of using the wave surface as a design method gives rise to a variety of possibilities to be employed for different piezoelectric materials depending on their crystal isotropy and c-axis orientations.

SUMMARY

The present inventive subject matter relates to the design work of circular CMOS-SAW devices.

The piezoelectric crystals that are employed for SAW devices are anisotropic in general. Anisotropic crystals cause SAW propagation characteristics to vary with direction. In order to obtain the maximum electromechanical conversion factor, the placement of IDTs on the substrates should be carefully examined. If a surface acoustic wave were to be propagated on an isotropic plane surface, its velocity would be the same in all propagation directions. This is not the case for SAW propagation on the plane surface of an anisotropic surface such as piezoelectric substrate. In this situation, the beam of elastic energy produced by the input IDT may not be along the propagation wavefront [2]. The solution to this problem is to apply beam steering which can be addressed by fabrication techniques. If the IDTs are misaligned with respect to the desired pure-mode axis, the receiving IDTs does not intercept the entire incident SAW beam, which gives rise to additional insertion loss [1]. Elimination of this problem requires careful crystal fabrication and correct alignment of IDTs based on the crystal structure.

Accordingly, provided herein is an integrated circuit chip having a "circular-design" SAW device as an on-chip component. In preferred embodiments, the chip can be a microprocessor, a programmable integrated circuit, a microelectromechanical system (MEMS), and a nanoelectromechanical system (NEMS).

In one embodiment, an integrated circuit chip is provided which has an embedded heater structure.

In another preferred embodiment, a SAW device having an absorber structure which comprise CMOS layers of metal1, metal2, and polysilicon is provided.

Also provided in a preferred embodiment is an LC circuit, or TANK circuit, which comprises a SAW device and an amplifier on the same chip. In another embodiment, a local oscillator is provided, which comprises an LC circuit connected to a Pierce oscillator.

SAW resonators fabricated using CMOS technology are also contemplated as within the scope of the invention.

Preferred processes for fabricating a SAW device using standard CMOS technology are also contmeplated, comprising the steps of: i) depositing piezoelectric material on top of SAW IDT's, and ii) performing a wet-etching of the piezoelectric material to expose the pads for bonding, wherein the SAW IDT's are patterned on the dialectic layer during CMOS fabrication and a reactive ion etch releases the IDT's from the dielectric layer before the piezoelectric material is deposited.

In preferred processes, the piezoelectric material is ZnO, the wet-etching uses a very dilute acid solution, and wherein the very dilute acid solution is a two acid mixture, wherein each acid of the two acid mixture is selected from the group consisting of acetic acid, hydrochloric acid, and phosphoric acid.

Additional preferred processes include wherein the CMOS process sequence includes fabricating an absorber structure on the SAW device designed from stacking CMOS layers of metal1, metal2 and polysilicon to achieve a surface higher than the IDT level for attenuating or reflecting the acoustic waves.

SAW devices made by the processes herein are also within the scope of the invention.

A heat control structure built within the substrate silicon during the CMOS process is also part of the inventive subject matter and can be be adopted in any of the CMOS chip devices herein. In preferred embodiments, the heat control structure is an n-well layer that has a TCR of 0.5-0.75%/K, which is the highest among various CMOS process layers and wherein the n-well provides an embedded heater structure that can directly control the temperature of the substrate and the mass sensitive area without causing any disturbance on the SAW delay line path or the IDT finger design.

Preferred uses of the devices herein include SAW based integrated circuit detection systems which comprise: a sensor having at least one sensing element for selectively combining with target molecules, said sensor generating a signal when combined with said target molecules responsive to incident electromagnetic radiation applied to said sensor/target combination; and an integrated circuit microchip to which the sensor is affixed, the integrated circuit microchip including: a plurality of detection channels operatively associated with said sensing elements, each of said detection channels including a detector for detecting electromagnetic signals, said detectors selected from the group consisting of photodiodes and phototransistors. In preferred uses the sensor comprises a chemical receptor, a bioreceptor, a polymer, a biopolymer, a molecular imprint polymer, a biomimetic, an antibody, an enzyme, a cell receptor, a molecular print assay, or a nucleic acid.

For detection of the target, phase shift detection or alternatively frequency shift detection can be used within the SAW device.

The systems herein can also preferably be implemented in a hand held unit. Thus, as oscillator or filter etc. or alternatively as a bio/chemical sensing device.

Provided is a process for fabricating a SAW device using CMOS technology, comprising: designing and fabricating a SAW IDT through a regular CMOS process sequence to obtain a SAW device; performing a reactive ion etch on the SAW device; performing a maskless sputtering from the front to the SAW device using ZnO, wherein the ZnO covers the entire surface including the IDT fingers and the exposed Si; etching the SAW device using a simple shadow mask, wherein the the mask is constructed using a Si, and wherein the photoresist build up covering the pad frame is completely removed by i) exposing the device after spincoating with a photoresist, applying developer, and ii) performing a second exposure and development to remove the excessive photoresist using the same exposure time and development time, and wherein the etching process is slowed using a very dilute acid solution.

The process can also include wherein the CMOS process sequence includes fabricating an absorber structure designed from stacking CMOS layers of metal1, metal2 and polysilicon to achieve a surface higher than the IDT level for attenuating or reflecting the acoustic waves.

The process also contemplates wherein etching the SAW device using a simple shadow mask comprises wherein the the mask is constructed using a square Si piece of size 2×2 mm, and wherein the photoresist build up covering the pad frame is completely removed by exposing the device for about 20 seconds after spinning a Shipley 1818 2:1 thinner for 40 sec at 5000 rpm, wherein a 2 min development in 5:1 Developer is applied, and performing a second exposure and development to remove the excessive photoresist using the same exposure time and development time, and wherein the etching process is slowed using a very dilute solution of a two acid mixture, wherein each acid of the two acid mixture is selected from the group consisting of acetic acid, hydrochloric acid, and phosphoric acid.

Another preferred embodiment of the invention includes a SAW device made by the processes described herein, especially those wherein signal control and processing circuitry are integrated on the same chip, and those wherein the n-well layer has a TCR of 0.5-0.75%/K, which is the highest among various CMOS process layers and wherein the n-well provides an embedded heater structure that can directly control the temperature of the substrate and the mass sensitive area without causing any disturbance on the SAW delay line path or the IDT finger design.

A further preferred embodiment includes a SAW based integrated circuit based detection system comprising: a sensor having at least one sensing element for selectively combining with target molecules, said sensor generating a signal when combined with said target molecules responsive to incident electromagnetic radiation applied to said biosensor/target combination; and an integrated circuit microchip to which the sensor is affixed, the integrated circuit microchip including: a plurality of detection channels operatively associated with said sensing elements, each of said detection channels including a detector for detecting electromagnetic signals, said detectors selected from the group consisting of photodiodes and phototransistors.

Preferably, the integrated circuit includes wherein the sensor comprises a chemical receptor, a bioreceptor, a polymer, a biopolymer, a molecular imprint polymer, a biomimetic, an antibody, an enzyme, a cell receptor, a molecular print assay, or a nucleic acid.

It is believed that advantages of the exemplary embodiments and/or exemplary methods of the present invention may include optimized biosensor devices, improved biosensor arrangement performance, determination of effective sensing media immobilization approaches, and SAW based biosensors that may be used to provide continuous, in-situ, and rapid detection and quantification of analytes in samples.

DETAILED DESCRIPTION OF THE PREFERRED EMBODIMENTS

CMOS is short for complementary metal oxide semiconductor. Pronounced see-moss, CMOS is a widely used type of semiconductor. CMOS semiconductors use both NMOS (negative polarity) and PMOS (positive polarity) circuits. Since only one of the circuit types is on at any given time, CMOS chips require less power than chips using just one type of transistor. This makes them particularly attractive for use in battery-powered devices, such as portable computers. Personal computers also contain a small amount of battery-powered CMOS memory to hold the date, time, and system setup parameters.

SAW (surface acoustic wave) devices are widely used as electronic filters, delay lines, resonators in today's communication systems. Although telecommunication industry is the largest user of these devices, SAW based sensors have many attractive features to be explored for emerging technologies in automotive (torque, pressure), medical (biosensor) and commercial (vapor, gas, humidity) applications.

Figure 1:
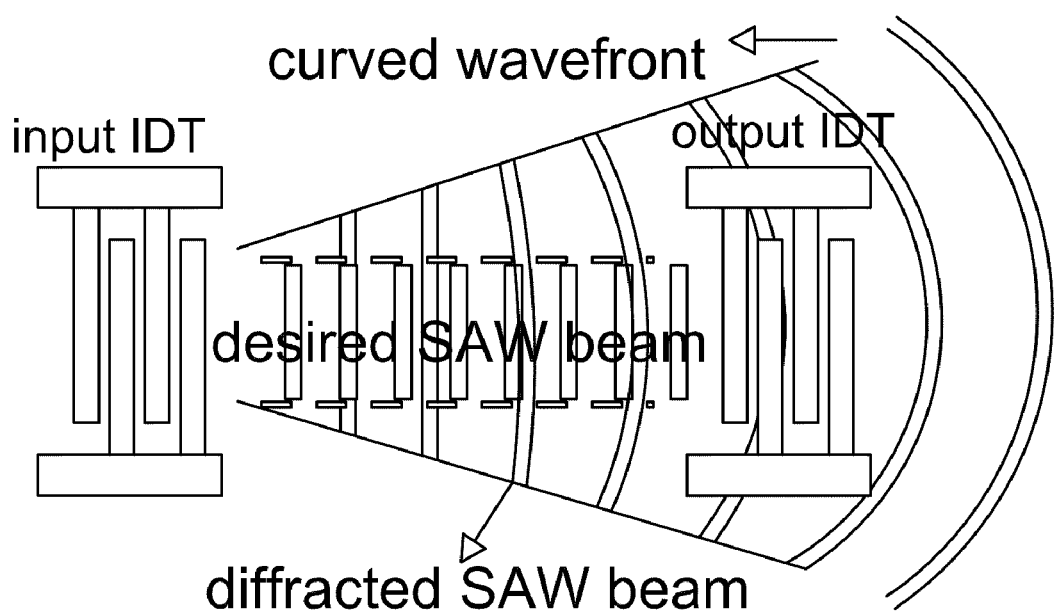
FIG. 1 is an illustration of a SAW diffraction pattern due to finite aperature.

Surface acoustic waves (both Rayleigh and pseudo-SAW) are generated at the free surface of a piezoelectric material. An application of a varying voltage to the metal IDT (interdigital transducer) generates the acoustic wave on the input side. In the basic configuration there is an input IDT and an output IDT. The acoustic wave generated by the input IDT travels through the region called the delay line and reaches the output IDT where the mechanical displacements due to the acoustic waves create a voltage difference between the output IDT fingers. One of the most widely used and interesting sensing mechanism that acoustic wave sensors employ is mass loading. Prominent applications are in film thickness monitoring, gas, liquid phase chemical sensing and biosensing. The delay lines of SAW devices are coated with some bio/chemical coating which selectively reacts with the entity under analysis. This interaction produces a shift in the resonant frequency of the SAW device. By measuring this shift in frequency domain, a detailed analysis of the entity being sensed can be completed. FIG. 1 depicts the basic principle of SAW based bio/chemical sensors employing the mass loading scheme.

Using a combination of IC compatible technologies, such as Si micromachining, thin film deposition, bio/chemical layer growth, integrated electronics, smart structures and systems can be realized. Considering the advantages that CMOS technology provides along with the ever-developing CMOS compatible MEMS processes, the SAW technology performance can be improved significantly. Therefore, an array of SAW delay lines were designed and fabricated through a regular CMOS process sequence, characterized and post-processed using widely used MEMS techniques.

New Circular Design SAW Device

The design, modeling and fabrication of a novel circular SAW (Surface Acoustic Wave) device in CMOS (Complementary Metal Oxide Semiconductor) are introduced. The results obtained in our previous work demonstrated that it is possible to design and fabricate SAW based sensors in CMOS with comparable performances to conventional devices. It is of great interest to improve the transfer characteristics and to reduce the losses of conventional rectangular SAW architectures for obtaining highly selective sensor platforms. Performance deficiencies of regular SAW devices in CMOS were addressed with this new architecture for improved performance. A 3D model for the novel architecture was constructed. A detailed finite element analysis was carried out to examine the transient, harmonic and modal behavior of the new architecture under excitation. The devices were fabricated in 0.5 um AMI Semiconductor technology and the post processing was carried out using cost effective CMOS compatible methods. The results demonstrate that it is possible to obtain highly oriented surface acoustic waves by using the novel circular architecture. A 12.24 dB insertion loss improvement was achieved when compared to a conventional rectangular device that was fabricated in the same technology.

Although it is stated that equivalent SAW propagation in every direction on piezoelectric substrates is not a common feature, the piezoelectric material that is used in our work, ZnO, presents a very small difference between the shear sound velocities propagating along [001] and [100] directions [12]. This property of ZnO makes it possible to assume isotropy for wave generation and propagation purposes.

Figure 2:
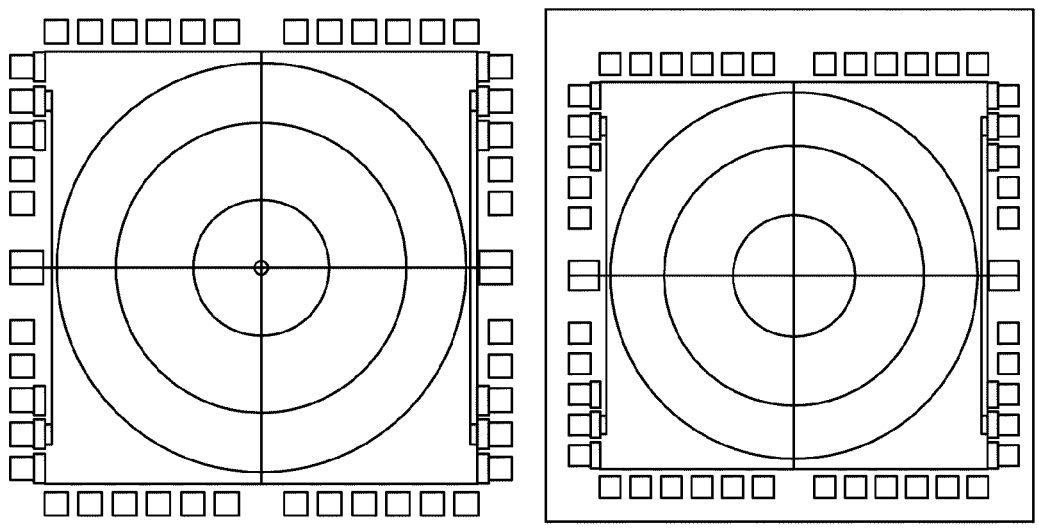
FIG. 2. (a) shows a layout top view for the novel circular SAW architecture completed in Cadence virtuoso layout editor. (b) shows a top view snapshot of the fabricated chip in AMI 0.5 micrometer 3-metal 2 poly technology.

In order to overcome the deficiencies caused by the diffraction of finite aperture, the strong directional dependency of the crystals, and to investigate the efficiency of fully concentric circular IDT structures in SAW medium, a novel architecture was developed. FIG. 2 depicts the layout of the new architecture alongside with the fabricated chip top view. This novel architecture consists of concentric circular IDT structures that are aligned on a common focal point. It addresses the previously listed deficiencies without using any of the methods listed in the literature. In contrast to the conventional rectangular SAW devices, the input and output IDTs are not physically equal in size. The input IDT? the outer circle fingers—are much larger in size than the output IDT? the inner circle fingers. This way, a smaller amount of input power is used to generate effectively the same acoustic wave as the conventional rectangular devices. Moreover, the reduction in the electromechanical conversion due to anisotropy is alleviated since the wave will be released from every possible angle of the crystal. The concentric nature of the novel architecture also eliminates the wave spreading problem due to finite aperture. Instead of spreading the wave on the delay line, it concentrates the acoustic waves to a focal point. Due to the circular nature of this architecture, the effective sensing area is also increased when compared to a regular rectangular delay line with the same dimensions. In addition, this architecture provides a spatially uniform sensitive surface for detection of any analyte that is introduced on the sensor area. These improvements that are suggested by the novel architecture are utilized to collectively increase the sensitivity of SAW based sensors in general.

Circular SAW Theory Background

In order to model the novel circular SAW devices, the equivalent circuit modeling based on Mason equivalent circuit was used as a starting point. The derivation of this equivalent circuit [1] and the application of it for CMOS—SAW devices were carried out in detail in our previous publications [13], [14]. This modeling approach applies only to conventional rectangular SAW IDT structures. Therefore, it should be expanded to include the circular nature of the devices in this work. For this purpose, a modified version of the AsoW theory is integrated into the Mason equivalent circuit model. This modification makes use of the total amplitude distribution and the wave vector definitions in determining the overall transfer function of the equivalent circuit.

Figure 3:
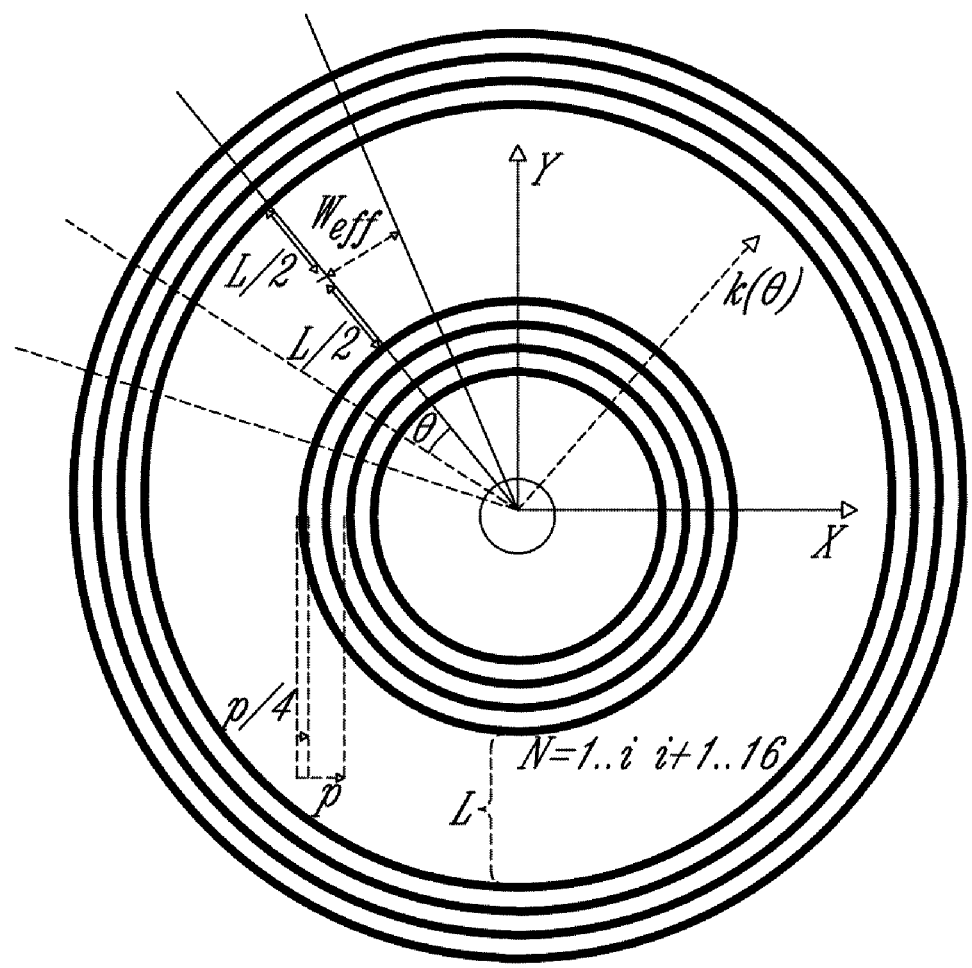
FIG. 3 shows circular SAW geometry and design parameters.

If the cut of the piezoelectric material is fixed, the wave vector k can be expressed as a function of propagation angle? [8]. The ZnO that is used in this research has a perfectly perpendicular c axis and provides an isotropic medium for wave vector purposes. Assuming no dispersion or propagation losses in the semi-infinite substrate, and a linear system, total amplitude distribution can be evaluated by the scalar field [15]:

$$\psi_T(X, Y) = \sum_{i=1}^{N} \frac{1}{2\pi} \int_{-\infty}^{\infty} \overline{\psi_i}(k_y) \exp[-j\{x_i k_x(k_y) + y k_y\}] dk_y \quad (1)$$

where xi is equal to 0,−p,−2p, . . . ,−Np and N is the finger number of IDT. kx and ky are the X and Y components of wave vector k(Θ) as depicted in FIG. 3. ψi(ky) is the inverse Fourier transform of the acoustic source function ψi(Xi, Y) and is provided by $$\overline{\psi_i}(k_y) = \int_{-\infty}^{\infty} \psi_i(X_i, Y) \exp(jYk_y) dY \quad (2)$$

where the acoustic source function $\psi_i(X_i, Y)$ is given by [8]

$$\psi_i(X_i, Y) = \begin{cases} C \cdot (-1)^{|X_i/p|} & |Y| < W/2 \\ \frac{C}{2} \cdot (-1)^{|X_i/p|} & |Y| = W/2 \\ 0 & |Y| > W/2 \end{cases} \quad (3)$$

Figure 4:
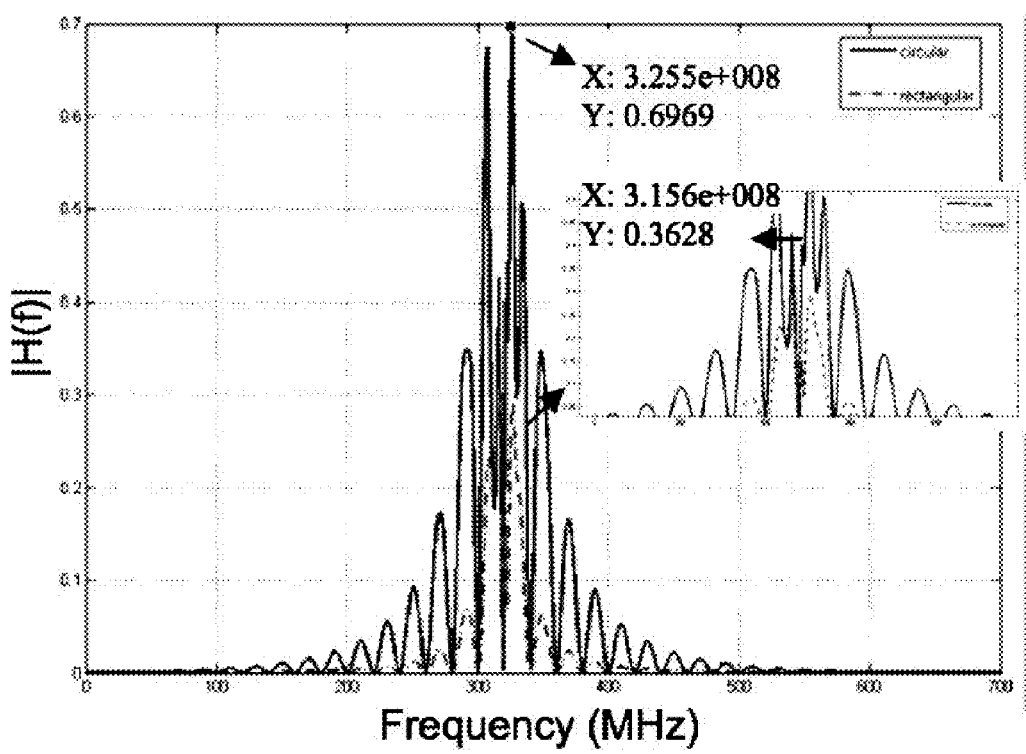
FIG. 4 is a graph showing simulated response for the crossed field based model of the circular device with angular correction. Conventional rectangular device response is superimposed for comparison. 6bB insertion loss improvement is observed.

In (3), W is the aperture of the IDT, C an arbitrary constant, and p is the period of the IDT as calculated in [13]. Equations (2) and (3) can be used to calculate the amplitude field of a conventional rectangular IDT such as the one laid out in our previous work [14]. In order to carry out a comparative performance analysis between the conventional rectangular and the novel concentric circular architectures, the same design parameters were selected for the circular device such as p=12 um with single electrode width of 3 um. FIG. 3 presents these important design parameters. To include the circular effect of the concentric architecture, the AsoW theory should be modified. The equivalent aperture method developed in [11] describes that a curved IDT can be approximated by a straight IDT with equiphase distribution. This approximation modifies the acoustic source function with the inclusion of an angular function factor by $$\overline{\psi_i^c}(X_i, Y) = \overline{\psi_i}(X_i, Y) \cdot \exp[jk_0 \cdot \Delta(X_i)] \quad (4)$$

where Δ(Xi) is the path difference between the real aperture and the equivalent aperture of the curved IDT. Expanding the angular equivalence to a 360 degree full curvature and approximating each infinitesimal arc per angle as a rectangular IDT, the novel concentric circular SAW device is modeled. The relevant geometry that is used to derive the total amplitude based circular correction and the pertaining wave vector is depicted in FIG. 3. The equivalent circuit derived in [1] is used to represent each infinitesimal element. Based on this derivation, the transfer function for each such element is found and corrected by the angular function factor of (4). By using the superposition principle, the transfer characteristics are obtained as formulated by $$|H(f)_{total}| = \sum_{m=1}^{360} |H_m(f)| \cdot \exp[jk_m \cdot \Delta(X_i)] \quad (5)$$

where Hm(f) is the input-output voltage transfer function for a conventional rectangular SAW device that was derived and applied in our previous work [13]. Note that, this function is an improved version of the fundamental H(f) from [1] and addresses finger reflections, and average velocity shifts due to high metallization ratio of these devices [14]. The effect of circular (angular) correction from (4) is incorporated in (5) to reflect the modification made on each infinitesimal circular arc element. FIG. 4 shows the resultant insertion loss improvement when compared to the conventional rectangular device. The circular architecture provides an insertion loss improvement of 6 dB. This improvement can be explained primarily due to the superposition of the effective equivalent wavefronts on the focal point. Another significant difference is the over expressed side lobes when compared to the conventional SAW transfer function. This can be explained by the accumulation of small differences in wave arrivals from the equivalent apertures of each infinitesimal IDT piece per angle. It is important to note that, this equivalence derivation is only valid for piezoelectric materials that have the wave velocity isotropy which is a reflection of the crystal isotropy as in the case of ZnO. Otherwise, the wave arrival differences would be expected to cause completely distorted output characteristics for the case of an anisotropic velocity distributions of other piezoelectric materials. The primary acoustic wave propagation in this work occurs in the ZnO layer. Although the multilayered structure (Si, SiO2, Al) would suggest a variety of possible crystallography (cubic, tetrahedral etc.) the waves are generated and contained in the piezoelectric layer. Therefore, the approximate full isotropy assumption holds true only for the ZnO layer.

Finite Element Modeling and Analyses

Equivalent circuit model provides a good starting point for designing SAW devices. The results obtained in the previous section allow the determination of the primary design parameters such as the center frequency, 3 dB bandwidth, insertion loss and transfer characteristics at and around the frequency of operation. However, it makes several approximations and assumptions to convert the acoustic properties to electrical representations. Although this approach provides a fast and relatively accurate analysis of the performance characteristics, it is always highly desirable to gain insight into the actual electromechanical interactions and the fundamental physics of acoustic wave generation or propagation. Therefore, in order to fully understand the acoustoelectric interactions that take place on the piezoelectric material and to closely investigate the behavior of the IDTs when designed in CMOS, a comprehensive finite element analysis (FEA) was carried out for the novel Circular SAW architecture that is presented in this research. The details of the 3D modeling and Finite Element (FE) Analyses methodology were laid out in our previous work [13], [14] for the case study of conventional rectangular devices. The same methodology and tools were applied to the case of the circular SAW architecture for comparative analyses of performance.

Figure 5:
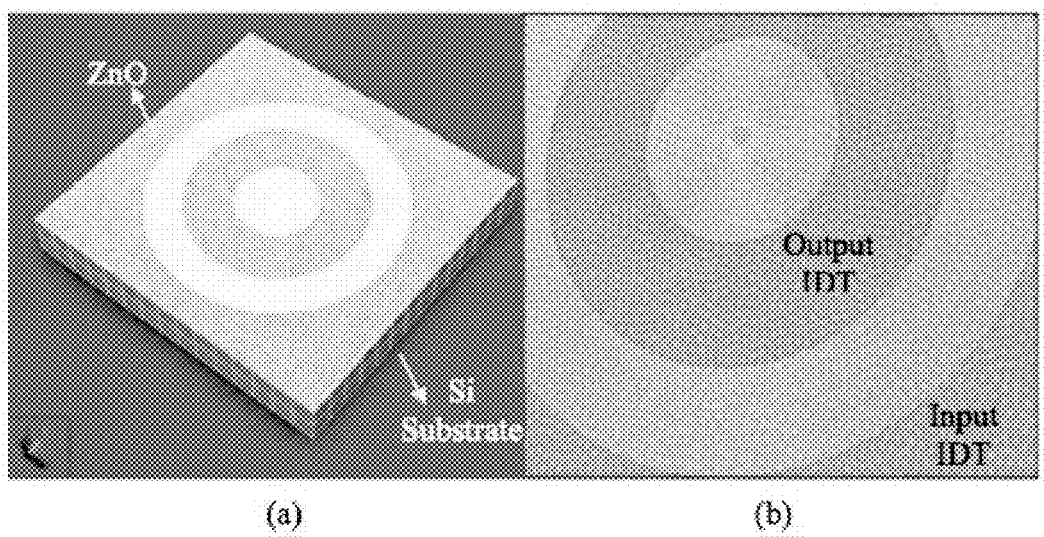
FIG. 5 (a) shows meshed circular SAW delay line with input/output IDT's and transparent display of top piezoelectric layer. (b) shows a close-up snapshot of the meshed IDT and the piezoelectric material with fine tetrahedron elements.

Coventor software toolset [16] was used to model the concentric circular SAW delay lines. After defining the 17 step CMOS process the 3D model is constructed. The meshed version of this 3D model is depicted in FIG. 5 (a). This model is used to apply all the boundary conditions that were used in testing and the material properties that were used in fabricating the devices. A fine tetrahedron type meshing was used to mesh the primary elements of interest, namely, the piezoelectric thin film, the metal IDTs and the oxide layers.

FIG. 5 (b) shows the finalized mesh structures for the listed layers. The final model meshing resulted in 168,860 faces and 75,555 volume elements. As in the case of the rectangular devices, transient, harmonic, and modal analyses were carried out. The major interest is in the steady state harmonic response of the piezoelectric material to the given excitation.

Figure 6:
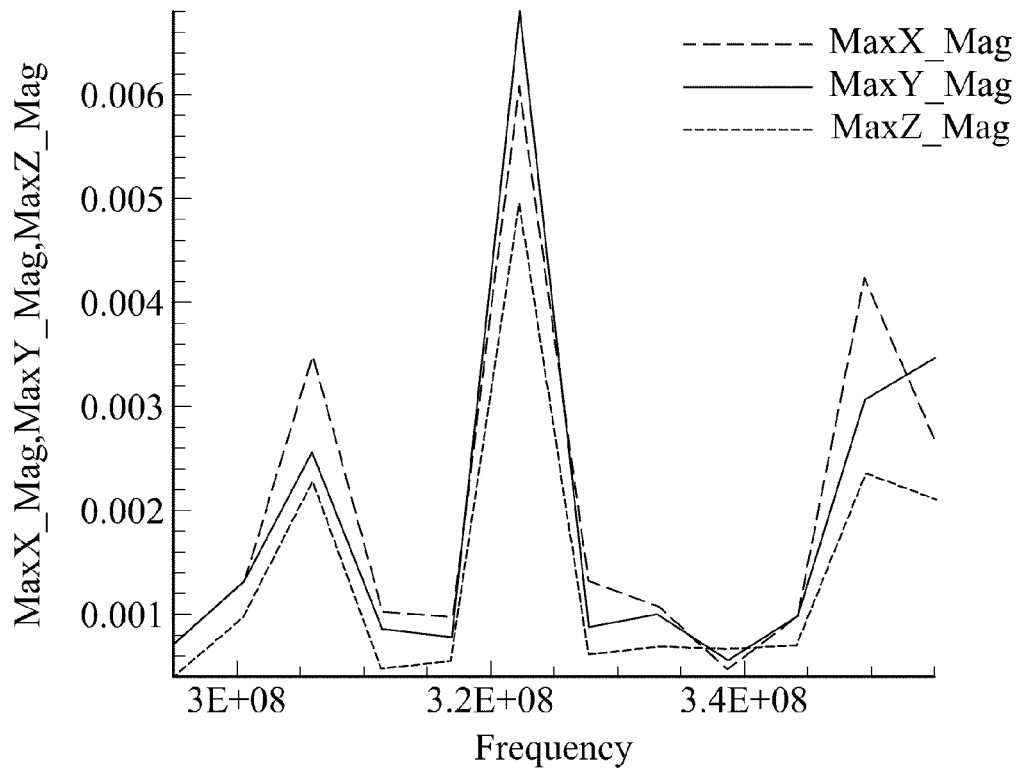
FIG. 6 shows harmonic displacements of circular SAW in frequency domain. The center frequency is found to be 321.8 MHz where the maximum displacement in all directions occur.

Therefore, an initial modal analysis should be run to determine the frequency of the modes and the generalized masses for respective modes. Using the same boundary conditions and mechanical solver settings, natural modal frequencies for the circular device is obtained. Table I lists down these frequencies alongside with their corresponding generalized mass figures. It also presents the maximum and minimum displacement figures for the steady state modal simulation. Mode 5 and Mode 3 provide the highest and lowest generalized mass figures respectively. The generalized mass associated with a certain mode is used in harmonic analysis, for which the equation of motion is formulated using the eigenmodes that are previously determined by modal analysis. The generalized mass associated with a mode i is computed by [16]

$$m_i = \Phi_i^N M^{NM} \Phi_i^M \quad (6)$$

where MNM is the mass matrix for the device under analysis and the superscripts refer to the degrees of freedom (DOF) of the FE model.? I represents the eigenvector for mode i. For harmonic analysis input excitation, all modal values are plugged into the solver as eigenmodes. However, the center frequency is picked as Mode 4 where the maximum displacements were observed to occur. Harmonic analysis is carried out to determine the actual center frequency value for steady state harmonic excitation. FIG. 6 shows the resultant harmonic response in frequency domain. The center frequency is found to be 321.8 Mhz. It is important to note that the harmonic analysis presented in FIG. 6 reflects the characteristics of the displacement vectors based on mechanical stress/strain solutions on and around the operation frequency as opposed to the electrical transfer characteristics obtained from the equivalent circuit in the previous section.

Therefore, in order to bridge this difference of medium for comparative analysis between the two methods, a transient analysis is required to translate these mechanical results into their electrical implications. As evidenced by the results of the crossed field and AsoW theory explained in the previous section, the FE model harmonic analysis also gives 12 folds higher displacement figures when compared to the rectangular devices analyzed in [13]. This is a direct result of the equivalent superimposed wavefronts that are concentrated on the focal center of the device. In order to demonstrate these wavefronts with their corresponding wave propagation, transient analysis was also carried out.

Figure 7:
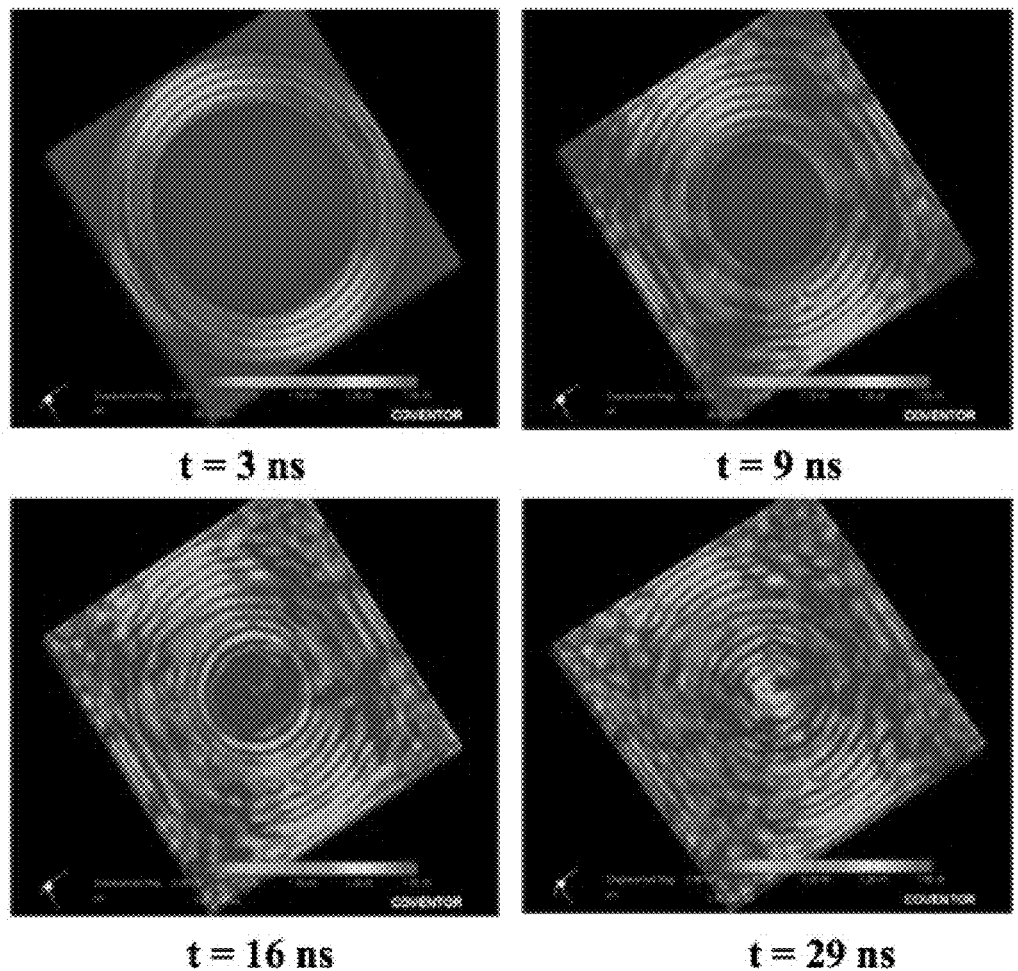
FIG. 7. Displacement vector distribution of the circular architecture for a transient simulation of 30 ns. The maximum displacement is obtained at the focal point of the output IDT.

The piezoelectric material properties obtained from tabulated data [17] and previous measurements [13], [14] were plugged into the material database to be reflected in the actual fabricated device simulation. A transient analysis of 30 ns was carried out with solver timesteps of 0.25 ns and output timesteps of 0.5 ns. A periodic sine wave input of amplitude 1 V was applied as the input excitation. Stress/strain, displacement, and wave/voltage propagation data were simulated. FIG. 7 shows the distribution of the displacement vectors in the ZnO layer for the 30 ns long simulation. Four discrete time snapshots were presented here for demonstration purposes. Duration of 30 ns seconds was selected to investigate the wave behavior even after the input excitation reaches the output IDT. As it is presented in the second step, the wave reaches the first finger pair of the output IDT at 8.6 ns which implies a velocity of 3488 m/s for a delay line length of 30 ?m. This velocity figure agrees closely with the acoustic velocity value of 3850 m/s that was used in calculations for ZnO. As can be seen from the wavefronts, the model used for the transient analysis is a scale down version of the actual fabricated device. This was imposed by the FEM tools to reduce computation time and resources. Therefore, a new downsized mesh was developed without disturbing or altering the integrity of the device layers, dimensions, and architectural parameters. This allowed the meshing and the simulations to converge more rapidly and be fully completed without any solver malfunction due to limitations of the underlying hardware resources. As evidenced by the distribution of the acoustic wave, the concentric circular wavefront is preserved as it is focused onto the focal point and the displacement vector reaches its maximum when it is exciting the output IDT. Although the circular device can be used in a symmetric fashion for its input/output IDT combination, in this research, the outer transducer is used to apply the input signal and the inner transducer is used to detect the output signal. Due to the size difference of these transducers, the effective impedance is reduced at the output port which in turn provides a higher efficiency for electromechanical conversion. It can also be observed that, there are wavefronts emanating away from the input IDT—outer circle—towards the square edges of the die. These diverging waves could possibly reflect from the square edges and contribute into unwanted distortion. However, since the inner circle is being employed as the output IDT for these devices, the outwardly diverging wavefront edge reflections can only arrive at the output IDT in a delayed fashion. This delayed distortion would only contribute in as secondary or higher degree harmonics which does not distort the passband characteristics. Moreover, as can be observed from FIG. 7, the square edges cause the diverging circular wavefronts to reflect as non-uniform dispersed waves that are much smaller in amplitude. Therefore, their overall contribution will be potentially negligible when compared to the combined first harmonics of actual wavefronts. This study draws a close agreement to the study of bending modes in circular quartz resonators by Leclaire et. Al [18] in which the (0,1) mode is also found to be such that displacement of the disk is nonzero everywhere on the edge.

Figure 8:
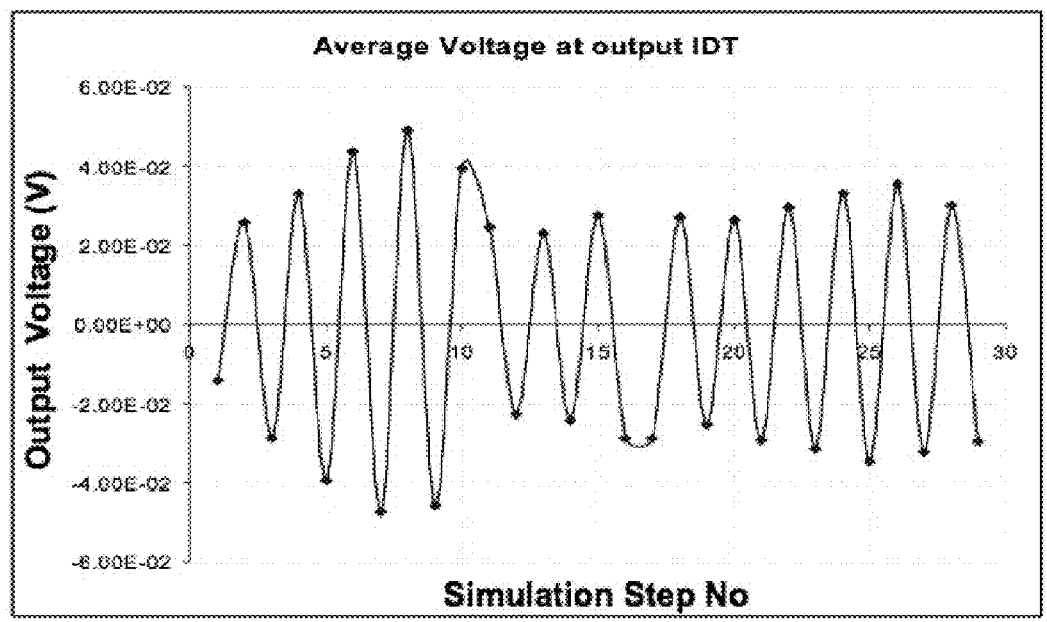
FIG. 8. Average voltage at the output IDT of the circular architecture. A 30 ns (each simulation step=1 ns) simulation shows the voltage induced at the output IDT. The maximum voltage is 0.055 V which translates into an insertion loss of −25.19 dB.

FIG. 8. Average voltage at the output IDT of the circular architecture. A 30 ns (each simulation step=1 ns) simulation shows the voltage induced at the output IDT. The maximum voltage is 0.055 V which translates into an insertion loss of −25.19 dB.

To obtain the effective insertion loss of the devices an output voltage analysis was also carried out. Average output voltage is extracted from the transient solver. FIG. 8 shows the resultant output voltage characteristics. The maximum voltage is determined to be 0.055 V which translates into an insertion loss of 25.1 dB. This yields an improvement of almost 10 dB with respect to the conventional rectangular devices.

Fabrication and Post Processing

Figure 9:
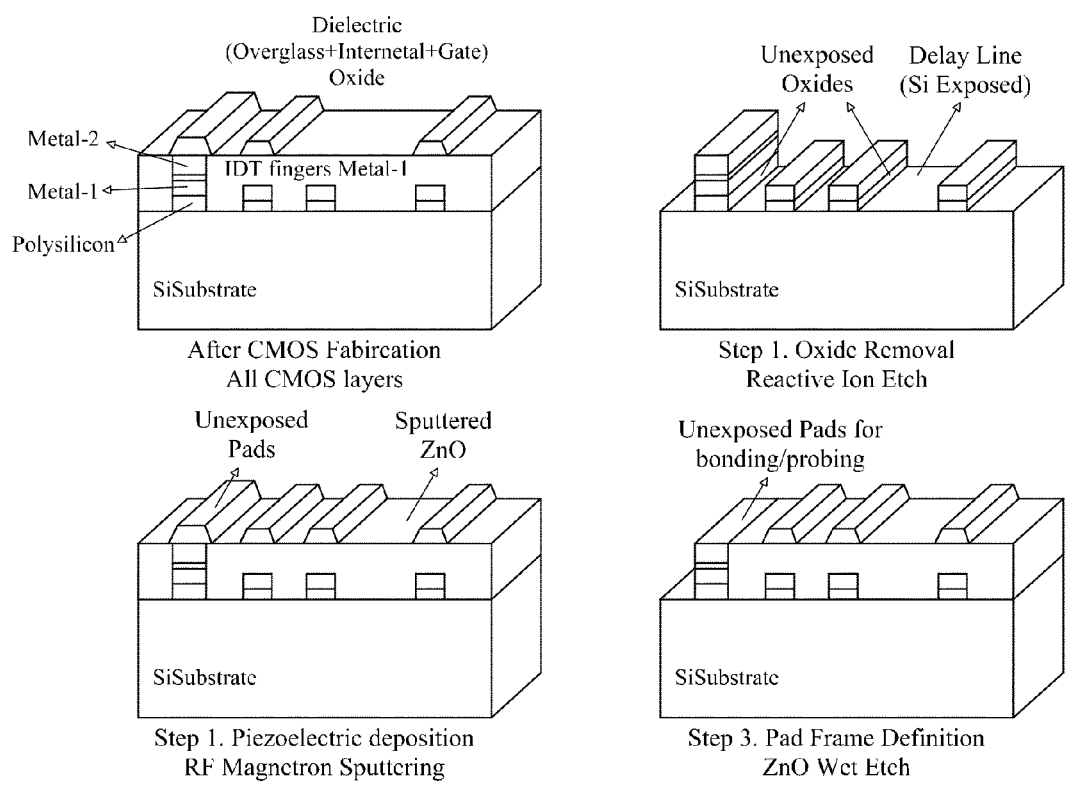
FIG. 9. Sketch of CMOS layers followed with the three step post processing sequence. Only the layers that are being utilized in the designs are depicted.

The Novel Circular SAW devices were fabricated in AMI 0.5 um 3 metal, 2 poly technology through MOSIS [7]. The layout of the devices employs ideas that are completely compatible with any other commercial CMOS process. Therefore, seamless migration to any other feature size as well as any other CMOS process can be easily achieved. The three step novel post processing methods were designed, tested, characterized and optimized in the previous work by the authors [13], [14]. The same sequence with minor adjustments was used for the post processing of circular SAW devices. The four steps of the sequence are summarized in FIG. 9. All three post processing steps are completely compatible with CMOS and do not disturb any of the CMOS layers. The sequence starts with the cleaning of the dice after the completion of CMOS fabrication. Trichloroethylene (TCE), Methanol and Acetone accompanied with ultrasonic agitation were used for this purpose. The first step of the post processing is the reactive ion etch (RIE) of the oxide layers.

The etching parameters are summarized in Table II. The RIE step was completed at UCSB Nano Fabrication Facility. The second step of the fabrication is the RF magnetron sputtering of the piezoelectric material of interest. In this work, ZnO was used as the piezoelectric thin film. The process parameters are listed in Table III. The ZnO sputtering was completed at Georgia Tech MSRCE Facility. The final step in the post processing sequence is the pad frame definition. The wet etch solution and recipe from [13] was used to complete this step.

Figure 10:
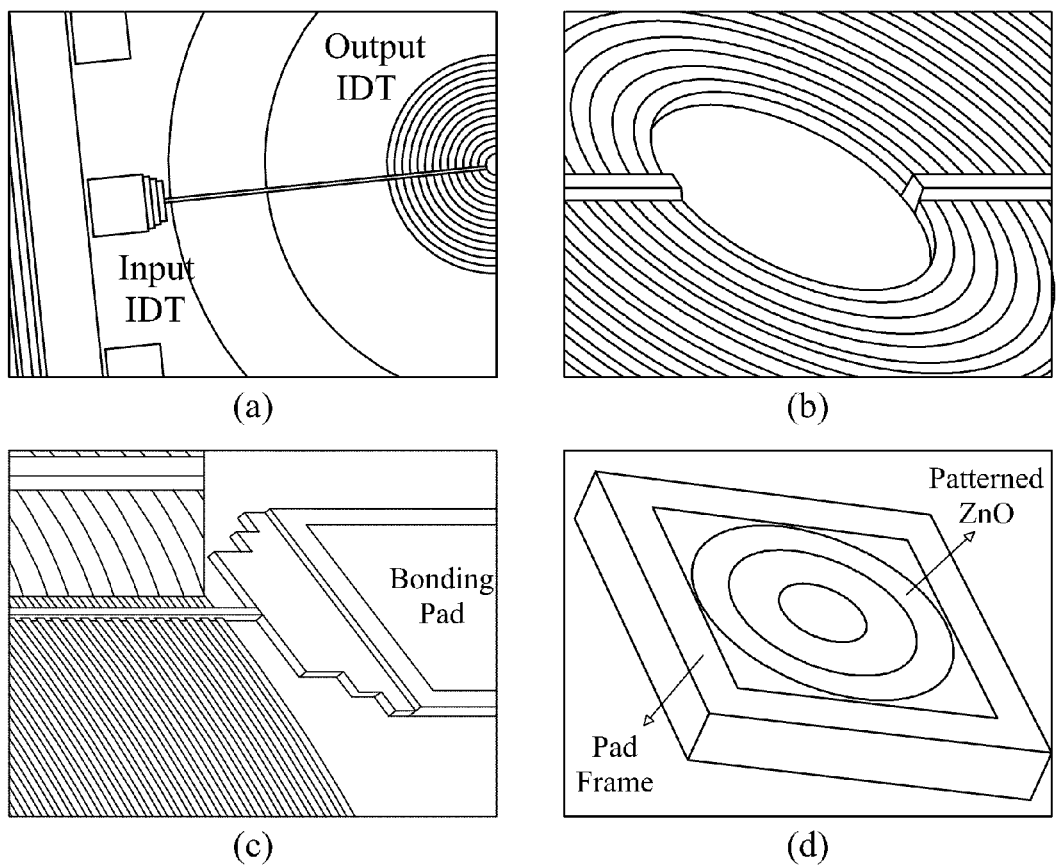
FIG. 10. (a) Top view SEM of the circular SAW chip after CMOS and before post processing (b) Close-up view of the inner IDT after RIE step with 90° sidewalls (c) Close-up view of the outer IDT with the pad after RIE (d) Top view SEM snapshot of the device after final step of ZnO patterning.

One of the major challenges of the post processing sequence is to obtain highly oriented perpendicular sidewalls between the IDT fingers for higher performance. This challenge was addressed by using RIE which employs the top metal layers as masking for the underlying oxides. Due to the anisotropic nature of this etching method, it was still applicable to the case of concentric circular fingers. This step provided highly oriented concentric IDT fingers without any loss of sidewall or connection metal integrity. FIGS. 10 (b) and (c) demonstrates the results of the RIE step. As can be observed from the figures, complete elimination of inter finger oxide layers was achieved. The die dimensions for rectangular SAW devices and the circular devices differ in considerable amounts. This was due to differences in the foundry dicing. Therefore, a new set of masks were designed for the last step of piezoelectric material patterning to accommodate the differences in the dimensions. Although there was a difference in the dimensions of the masking layers, the same procedure can be applied to pattern the ZnO layer and open up the pads for electrical contact. FIG. 10 (d) shows a typical circular CMOS-SAW die after the last post processing step is completed. A fully accessible clean pad frame that is free of any ZnO residue is obtained.

Figure 11:
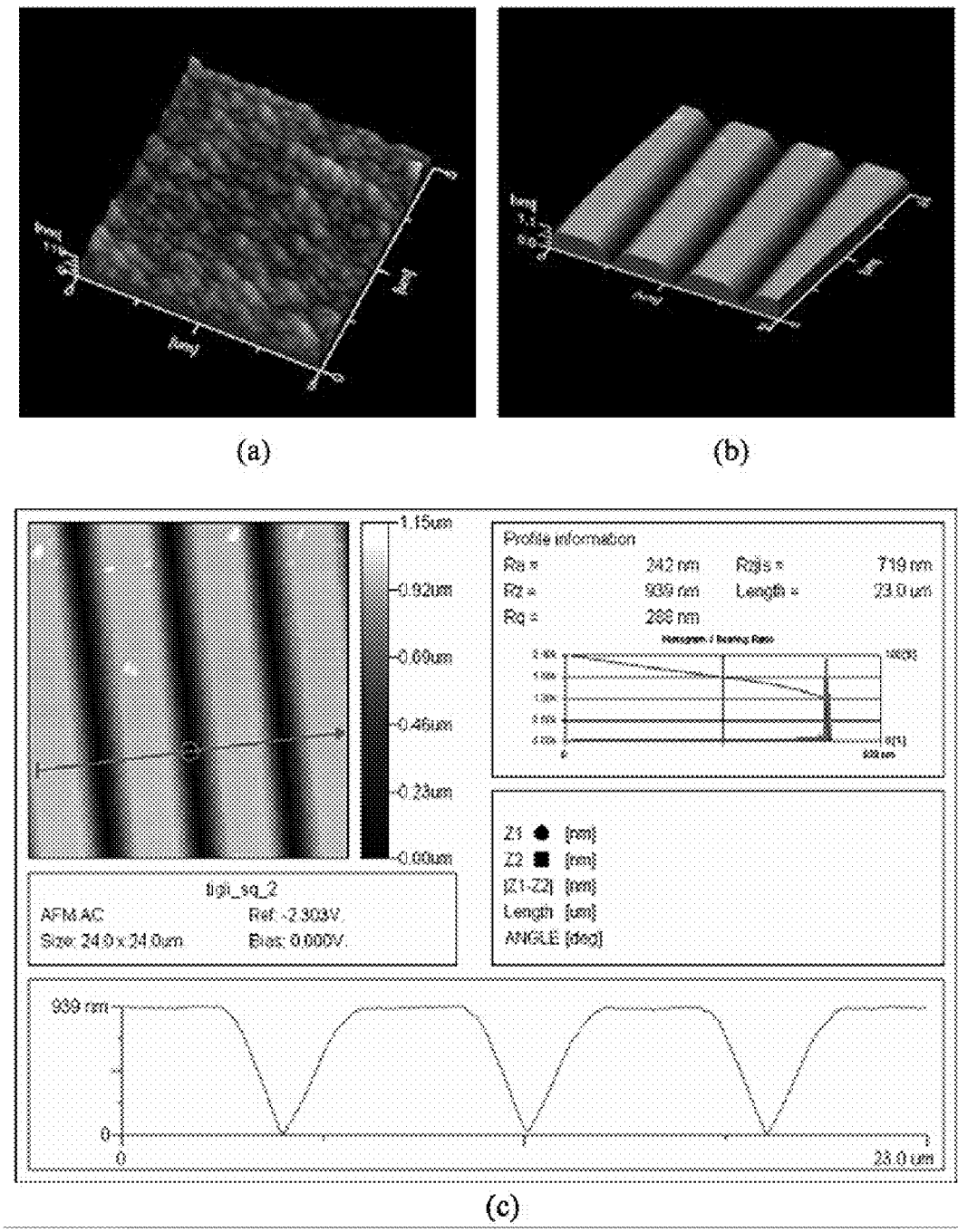
FIG. 11. (a) Close up for a 5 μm×5 μm revealing the grain size/surface roughness of ZnO on the delay line (b) 3D snapshot showing the ZnO on the IDT fingers (c) Surface profile showing average depths of ZnO on the IDT fingers for a scan area of 24 μm×24 μm.

A rough piezoelectric film surface causes reflections and hence propagation losses. Therefore, a smooth ZnO surface with the least possible surface roughness and small grain size is highly desirable. In order to obtain information regarding the surface roughness and grain size, JEOL High Vacuum Integrated STM/AFM/JSPM-5200 was utilized. 3D visualizations, profile histograms, and grain size measurements were taken for all the samples at two primary locations; one on the delay line ZnO and the second one on the IDT fingers. FIG. 11 summarizes the results for these locations of interest. As presented in FIG. 11 (a), the ZnO on the delay line shows a maximum grain size of 82.5 nm, which translates into an extremely smooth surface when compared to the reported 0.5-1 um for high-mobility samples and 200 nm for low mobility samples [19]. More importantly the grain size distribution histogram shows a peak around 25 nm for an area of 25.7 um2 with a balanced bell curved extension on both ends of the spectrum. As can be seen in FIG. 11 (b) ZnO deposition extended on top of the IDT fingers without losing its low surface roughness values that were attained on the delay line. Moreover, careful analysis from FIG. 11 (c) shows that a 939 nm of inter-finger ZnO depth translates into an effective ZnO bulk depth of ~3.061 um in the total 4.0 um sputtered ZnO. This depth provides an abundance of crystal structure where the wave energy is primarily confined to the 10% of the wavelength depth. In the case of the circular SAW devices the wavelength is 12 um, and most of the energy is primarily confined to the top 1.2 um of the piezoelectric material.

Results and Discussion

The major subjects of interest for performance analysis of SAW devices are the transmission coefficient and the reflection coefficient versus frequency. HP 8712ET, 300 kHz-1300 Mhz, RF Network Analyzer was used for analyzing the performance of the CMOS SAW devices. An enhanced response calibration was carried out in order to measure and compensate for the losses and errors due to the connector, cable irregularities and substrate losses. Cascade RF microprobes in GSG configuration were used to measure the transmission, reflection and phase responses. To determine the performance improvements and to provide comparative analyses, conventional rectangular CMOS SAW devices were characterized as well as the novel circular devices.

The rectangular CMOS-SAW devices are comprised of two identical delay lines that are placed on perpendicular axes. The period $\lambda=12$ um and the delay line length Lrect=600 um for these devices. Table IV summarizes the pertaining device dimensions for both circular and rectangular SAW designs.

Figure 12:
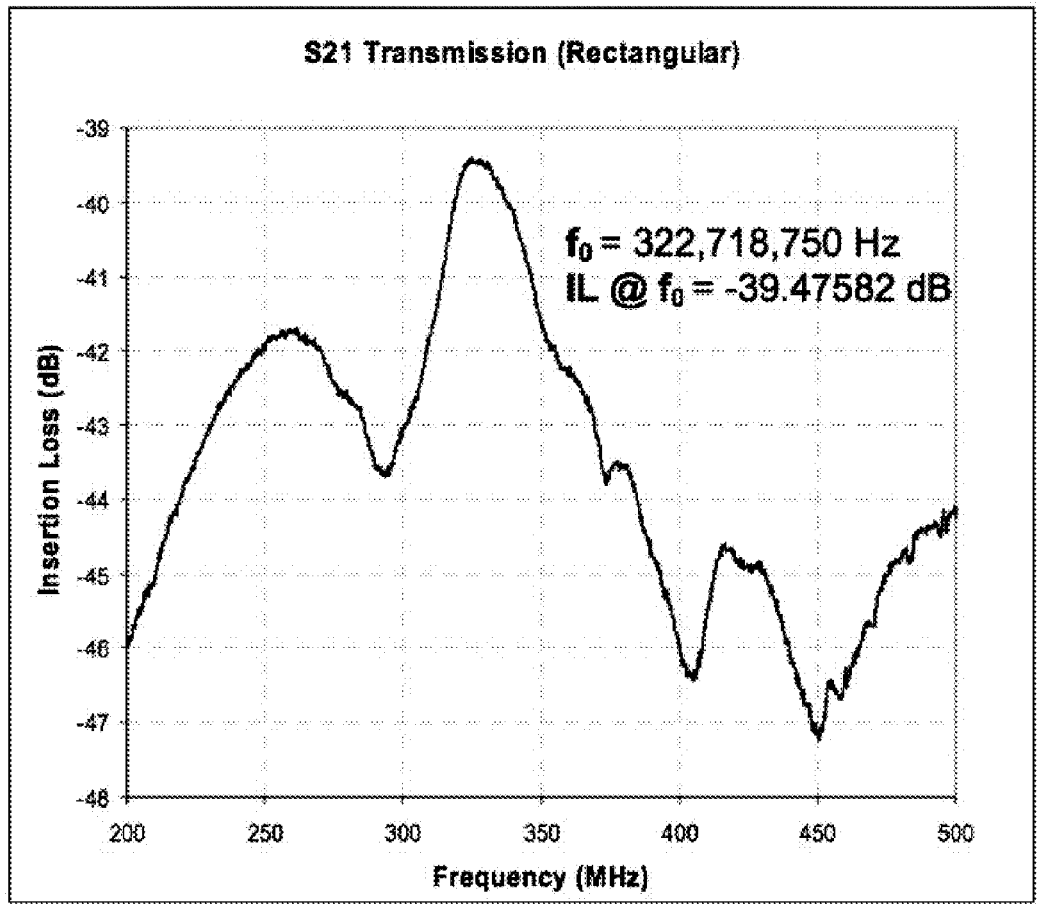
FIG. 12. Typical S21 Transmission transfer characteristics for the conventional rectangular devices. The center frequency is 322.718 MHz with an insertion loss of −39 48 dB FIG. 13. S21 Transmission transfer characteristics for a typical circular CMOS-SAW device. The center frequency is 323.16 MHz with an insertion loss of −27.23.

FIG. 12 presents a typical S21 Transmission transfer characteristics of the conventional rectangular device. Note that the design under test in these measurements are reference CMOS-SAW devices before any sensor processing is carried out. Therefore, it primarily reflects the ZnO—SiO2-Si multilayered device operation. The center frequency value closely agrees with the simulated and calculated values. Table V summarizes the results in comparison. As can be seen from the table, for the most important performance metrics experimental results and the FEM simulation results show close agreement with a 0.87% deviation in center frequency.

Although secondary metrics such as maximum rejection bandwidth and shape factor are typically investigated for RF filter design, they are presented in this table to show that the finite element and equivalent circuit models effectively reflect the actual performance of CMOS-SAW devices in design phase for sensor applications as well. In the case of sensor applications, a reproducible transfer characteristic with well defined center frequency and insertion loss is desired. The deviations in these metrics can be explained by a variety of fabrication, post processing and ambient variations. However, the most influential fabrication variation on the center frequency is the targeted ZnO thickness. The variation for the measured ZnO thickness is +/-8.333% with a standard deviation of 0.534, which translates into a maximum variation of 0.332 um for a 4 um target thickness in this work. This variation shifts the effective velocity on the dispersion curve causing the center frequency to be higher than the finite element and equivalent circuit models both of which use ideal and fixed fabrication conditions.

Figure 13:
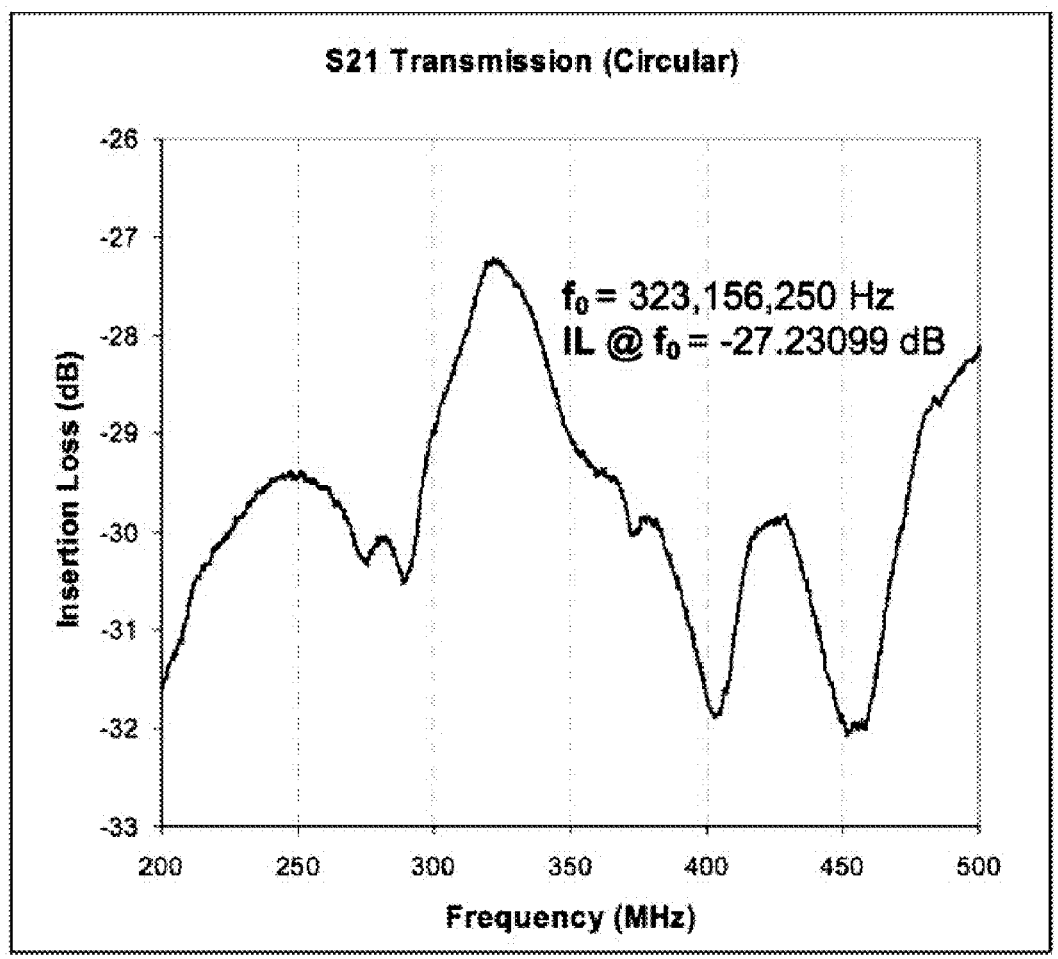

In the experimental device characterization phase, fabricated circular CMOS-SAW devices are also tested for comparative performance analysis. FIG. 13 depicts the S21 transmission transfer characteristics of a typical circular CMOS-SAW device before any sensor processing is conducted. As it is clearly seen from the insertion loss behavior, the circular device provides an insertion loss improvement of 12.24 dB. The FEM simulations predicted this improvement to be approximately 10 dB which closely agrees with the experimental result. Although the circular device provides better close in side lobe rejection, it has a larger 3 dB bandwidth when compared to the rectangular results. This is explained by the difference in the delay line length of two devices. The circular device employs an effective delay line length of Lcirc=250 um as opposed to rectangular delay line length of Lrect=600 um. This decrease in delay line length causes the mode distance to increase. Hence, the bandwidth will also increase because of this effect. This is due to the fact that the distance covered by the waves launched by the electrodes closest to the receiving IDT suffers less reflections and propagation losses which implies a shorter delay time [20]. A comparative performance metrics analyses between the equivalent circuit, finite element model and the experimental results is desirable. Table VI presents these metrics in comparison. The FEM simulation center frequency result show a 0.42% deviation from the experimental results which suggests a much closer agreement than the rectangular CMOS-SAW device case. The other performance metrics also show closer agreements with their experimental counterparts. The only parameter that suffers a large discrepancy is the insertion loss of equivalent circuit model. This discrepancy can be explained by the simplistic modeling and ideal conditions which are based on assumptions that ignore various sources of losses. However, the equivalent circuit model provides rapid design dimension extraction. On the other hand, FEM analyses result in more robust, detailed and concrete SAW performance investigation during the design phase. However, this is in the expense of time for development cycle. Therefore, depending on the requirements in the design phase, either method can be favored. Another important observation can be made by comparing the results with our previous work [13], [14]. The circular and the rectangular devices that were compared in this work were fabricated and characterized by using the same methods. The devices of the previous work comprised of another technology (AMI 1.5 um) and the finished devices were packaged on DIP-40 packages for testing as opposed to the package free RF microprobe/cable based testing of this work. Moreover, the data obtained in the previous work reflected simple test structures with much shorter delay line paths which essentially reduced the losses. The calibration models for the package pins and the surrounding wiring were not incorporated in the results of the packaged devices which also contributed in seemingly better loss results. However, in this current work, calibration models for every measurement setup component (wires, microprobes, and connectors etc.) were calculated and incorporated in the final measurements. Therefore, this method of testing proved to be more reliable and robust in terms of measurement integrity.

EXAMPLE

Chemical Sensors

SAW devices are extremely sensitive to tiny mass changes, detecting 100 pg/cm$^2$—less than 1% of a monolayer of carbon atoms. When coated with a chemically selective thin film, the SAW device is rendered sensitive to chemicals that interact with the film. Sensors based on surface acoustic wave (SAW) devices are being developed to detect a wide range of chemicals. The SAW device is an extremely sensitive gravimetric detector that can be coated with a film to collect chemical species of interest. Based on these devices, sensor systems have been developed that can detect trace (ppm to ppb) levels of airborne contaminants. Applications include weapon state-of-health, environ-mental, and non-proliferation monitoring.

Chemical species that have been distinguished as capable of detection up to 96% accuracy include the general categories of organophosphonate (DIMP, DMMP); chlorinated hydrocarbon ($CCl_4$, TCE); ketone (acetone, MEK); alcohol (methanol, n-propanol, pinacolyl alcohol); aromatic hydrocarbon (benzene, toluene), saturated hydrocarbon (n-hexane, cyclohexane, i-octane); and water.

During the manufacture of analyte detection chips, a sensor material is placed on the substrate. This sensor material may be deposited, coated, or otherwise applied on the substrate. In one embodiment, the sensor material is any material which provides an electrical response to an analyte. For example, an electrical response may be quantified in terms of impedance (Z), resistance (R), inductance (L), capacitance (C), or other electrical property. In an embodiment, the sensor material may be a polymer. The material may be organic, or inorganic in other embodiments. Further, the sensor material may consist of regions of a nonconductive organic material and a conductive material. In other embodiments, the sensor material may be insulating organic films that act as capacitors or composite films that act as inductors. A more detailed description of some sensor materials and their properties is discussed in U.S. Pat. No. 5,571,401. However, the present invention is not limited to the sensor materials in U.S. Pat. No. 5,571,401 since other materials may also be used.

In a specific embodiment of the present invention, the sensor technology may involve a series of conductive polymeric composite vapor sensors. The presence of an analyte may be detected through a change in, for example, the electrical resistance of a chemically sensitive carbon-based resistor. As discussed above, changes in electrical properties other than resistance may also be used; these include the evaluation of capacitive and inductance changes.

Further, the sensor material may be composed of conductor and insulator composites. This material may be placed on the substrate in a film. The organic nonconducting polymer of the composite absorbs the analyte (which may be a vapor). This induces a change in the electrical properties of the sensor material. The sensor material may also undergo physical changes such as swelling. When the analyte is removed, any changes in the electrical properties reverse. For example, the resistance, capacitance, and inductance may return to their original value. Any physical changes would also reverse. The response of these types of sensors are reversible over multiple analyte exposures as well as reproducible over a large number of trials under a variety of ambient atmospheric conditions. Therefore, a device fabricated using these types of sensor materials would have a relatively long service life.

In the case of using a composite such a nonconducting polymer and carbon black, the sensor material will be temperature sensitive. When using temperature-sensitive sensors, the sensor should be kept at a relatively constant temperature to provide relatively consistent results. For example, a temperature such as about 5 degrees C. above the ambient should provide good results. Further, extremely high temperatures, say, above about 100 degrees C., should be avoided since these temperatures would destroy the polymer sensor material or rapidly decrease its service life. For this reason, it is not expected that nonconducting polymer materials are to be used in the specialized environment of extreme high temperatures, say, from about 300 degrees C. to about 400 degrees C. or even higher. The polymer sensor materials will be usable in the normal temperature ranges from about 0 degrees C. to about 100 degrees C.

Using a conductor and insulator composite for the sensor material permits a very broad, diverse collection of sensor materials. For example, any conducting element including carbon blacks, metallic colloids, or organic conducting polymers, and combinations of these, may be used as the conductive phase of the sensors. Any organic material may be used as the insulating phase of the sensors. Furthermore, an advantage of these types of sensor materials is that they do not have the stability limitations of conducting organic polymeric materials. A conductor and insulator composite also does not suffer the limitations from the types of substituents or restrictions on the ranges of swelling variations that can be obtained from backbone modification of pure organic conducting polymers.

After processing of a substrate or wafer is complete, the wafer is tested to determine the number and location of the "good die." The percentage of good die on one wafer compared to the total number of die on the wafer is referred to as the "yield." Individual analyte detection dies are separated by sawing along the scribe lines. The analyte detection dies are then packaged, and may be further tested to ensure their proper operation. These dies may be packaged in a variety of packaging material including ceramic, epoxy, plastic, glass, and many others. Packaged analyte detection die may very much resemble packaged integrated circuit chips. For some types of applications, nonporous, nonreactive materials like ceramic may be used.

In one embodiment, the sensor material is deposited or applied at the wafer level, before individual dies are separated. In other embodiments, the sensor material is applied after the dies are separated.

EXAMPLE

Biological Sensors

Surface acoustic wave devices as biosensors are also well suited for the detection of biological agents. Positioning a receptor between IDT fingers to induce a phase shift or within IDT fingers to induce a frequency shift allows for electronic detection of bioagents. These devices have the dual advantages of high sensitivity, down to picograms/cm2, and high specificity, conferred by biological receptors such as antibodies, peptides, and nucleic acids. Detection of bacteria, viral particles, and proteins has been shown with these types of sensors. Handheld biodetection systems incorporating these microsensors are contemplated as within the scope of the invention.

The surface acoustic wave biosensor arrangements may be used for real time sensing and for quantifying the levels of bacteria, e.g. *Escherichia coli*.

Many monoclonal antibodies with high affinity and specificity for particular bacteria are available from commercial sources as well as the American Type Culture Collection (ATCC). For example, one of these antibodies, the ATCC HB-8178 antibody, may bind with the *E. Coli* pilus with high specificity and affinity. Any known coupling chemistry may be used for binding the monoclonal antibody to the sensor chip surface.

It may also important to optimize the chemical linking of the antibody, as well as the loading density. Independent fluorescence assays of the antibody density on the chip may be done using fluorescence labeled anti-IgG. The chip may be incubated in phosphate buffered saline with fluorescein labeled anti-IgG, and may then be washed with a buffer solution of increasing ionic strength to dislodge unbound antibody. The chip may then be scanned using a Perkin Elmer LS50B fluorescence spectrophotometer, and the bound antibody density may be calculated using FL-Winlab software, which may also calculate various parameters (such as, for example, the statistical variability observed in the surface loading between regions on the chip sample surface). This technique may be used to determine which of the coupling chemistries yields the best loading of antibodies.

Biological detection may include detecting of smaller molecular weight molecules as well as larger protein molecules, amino acids, and nucleic acids.

Current generated per analyte molecule bound to the biosensor surface may be compared to the response obtained from control. Analyzing the differences in the biosensor response may be useful for improving the chemistry and spatial properties of the biosensor arrangement to enhance its performance against the analyte of interest.

There are a number of U.S. patents which describe integration of a biosensor chip into a biosensor device, including U.S. Pat. Nos. 6,937,052, 6,743,581, 6,657,269, and 6,448,064, all incorporated herein in their entirety. Other U.S. patents describe the use for detection of a chemical, including U.S. Pat. Nos. 6,627,154, and 6,495,892, incorporated herein in their entirety.

REFERENCES

[1] C. K. Campbell, ?Surface Acoustic Wave Devices for Mobile and Wireless Communications,? Academic Press Inc., San Diego, Calif., Chap. 4, pp. 114-122, 1998.

[2] M. R. T. Tan, C. A. Flory, ?Minimization of Diffraction Effects in SAW Devices Using a Wide Aperture,? in Proc. IEEE Ultrason. Symp., November 1986, pp. 13-17.

[3] G. W. Farnell, ?Elastic Surface Waves,? in H. Matthews (ed.) ?Surface Wave Filters,? John Wiley and Sons, New York, Chap. 1, 1977.

[4] Y. Nakagawa, ?A New SAW Convolver Using Multichannel Waveguide,? in Proc. IEEE Ultrason. Symp., December 1991, pp. 255-258.

[5] J. B. Green, G. S. Kino, T. Khuri-Yakub, ?Focused Surface Wave Transducers on Anisotropic Substrates: A Theory Developed for the Waveguided Storage Correlator,? in Proc. IEEE Ultrason. Symp., November 1980, pp. 69-73.

[6] J. Z. Wilcox, R. E. Brooks, ?Time-Fourier Transform by a Focusing Array of Phased Surface Acoustic Wave Transducers,? J. Appl. Phys., vol. 58, no. 3, pp. 1148-1159, September 1985.

[7] R. E. Brooks, J. Z. Wilcox, ?SAW RF Spectrum Analyzer/ Channelizer Using a Focusing, Phased Array Transducers,? in Proc. IEEE Ultrason. Symp., pp. 91-95, October 1985.

[8] T-T. Wu, H-T. Tang, Y-Y. Chen, P-L. Liu, ?Analysis and Design of Focused Interdigital Transducers,? IEEE Transactions on Ultrasonics, Ferroelectrics, and Frequency Control, vol. 52, no. 8, pp. 1384-1392, August 2005.

[9] D-H. Qiao, C-H. Wang, Z-Q. Wang, ?Focusing of Surface Acoustic Wave on Piezoelectric Crystal,? Chinese Physics Letters, vol. 23, no. 7, pp. 1834-1837, July 2006.

[10] R. S. Fang, S. Y. Zhiang, ?SAW Focusing by Circular-Arc Interdigital Transducers on YZ-LiNbO3,? IEEE Transactions on Ultrasonics, Ferroelectrics, and Frequency Control, vol. 36, no. 2, pp. 178-184, March 1989.

[11] M. S. Kharusi, G. W. Farnell, ?On Diffraction and Focusing in Anisotropic crystals,? in Proc. IEEE, vol. 60, no. 8, August 1972, pp. 945-956.

[12] U. Ozgur, Y. I. Alivov, C. Liu, A. Teke, A. Reshchikov, S. Dogan, V. Avrutin, S. J. Cho, H. Morkoc, ?A Comprehensive Review of ZnO Materials and Devices,? J. Appl. Phys., vol. 98, no. 041301, pp. 1-103, August 2005.

[13] O. Tigli, M. Zaghloul, ?A Novel SAW Device in CMOS: Design, Modeling and Fabrication?, IEEE Sensors Journal, vol. 7, no. 2, pp. 214-223, February 2007.

[14] O. Tigli, M. Zaghloul, ?Design and Fabrication of a Novel SAW Biochemical Sensor in CMOS?, IEEE Sensors Conference, Special Session: CMOS Based Sensors, Invited Talk, Irvine, Calif., October 2005.

[15] D. P. Morgan, ?Surface Acoustic Wave Devices for Signal Processing,? New York: Elsevier, pp. 129-155, 1985.

[16] [Online] CoventorWare, ?Using CoventorWare, Analyzer Tutorial?. Available: http://www.coventor.com.

[17] Y. Min, ?Properties and Sensor Performance of Zinc Oxide Thin Films,? PhD Thesis, Massachusetts Institute of Technology, MA, 2003.

[18] P. Leclaire, J. Goossens, L. Martinez, N. Wilkie-Chancellier, S. Serfaty, C. Glorieux, Study of the Bending Modes in Circular Quartz The references above are incorporated herein in their entirety if necessary to enable the making and using the presently claimed inventive subject matter and/or to assist the definition of the level of ordinary skill in the art.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

TABLE I

MODAL ANALYSIS RESULTS FOR CIRCULAR SAW

| Mode Number | Frequency (MHz) | Generalized Mass (kg × $10^{-10}$) |
|---|---|---|
| 1 | 319.976 | 1.334938 |
| 2 | 319.997 | 1.811938 |
| 3 | 319.996 | 1.245447 |
| 4 | 320.008 | 2.983624 |
| 5 | 320.025 | 3.5846095 |

| Node Name | Maximum Displacement (normalized to 1 m) | Minimum Displacement (normalized to 1 m) |
|---|---|---|
| X | $2.573265 \times 10^{-5}$ | $-1.413531 \times 10^{-6}$ |
| Y | $2.855875 \times 10^{-5}$ | $-1.102223 \times 10^{-5}$ |
| Z | $2.701833 \times 10^{-3}$ | $-1.575299 \times 10^{-3}$ |

TABLE II

RIE STEP PROCESS PARAMETERS

| Gas in Use | Flow Rate | ICP Power | Etching Pressure | Sample Bias Power | Sample Temperature |
|---|---|---|---|---|---|
| $CHF_3$ | 40 sccm | 900 W | 37.5 mTorr | 200 W | 15° C. |

TABLE III

RF MAGNETRON SPUTTERING PROCESS PARAMETERS

| Gas in Use | RF Power | Sample Rotation | Sputterer Pressure | Target Thickness | Deposition Time |
|---|---|---|---|---|---|
| Ar/O$_2$ 50/50% | 150 W | 0.3 Hz | 5 mTorr | 4 μm | 13:15 hr:min |

TABLE IV

CMOS-SAW DEVICE PARAMETERS

| | | Circular | Rectangular |
|---|---|---|---|
| Period | p (μm) | 12 | 12 |
| Finger spacing | p/4 (μm) | 3 | 3 |
| Finger width | p/4 (μm) | 3 | 3 |
| Aperture | W (μm) | 2350 | 100 |
| Delay line length | L (μm) | 250 | 600 |
| Number of finger pairs | N | 16 | 16 |
| Die size | S (μm$^2$) | 1400 × 1400 | 1500 × 1500 |
| Number of IDTs on a die | M | 2 × 1 | 2 × 2 |

TABLE V

COMPARATIVE DEVICE CHARACTERISTICS OF RECTANGULAR SAW

| | Equivalent Circuit | FEM Sim. | Experimental |
|---|---|---|---|
| Center Frequency f$_0$ (MHz) | 318.4 | 320 | 322.7 |
| Insertion Loss at f$_0$ (MHz) | −9.11 | −32.76 | −39.48 |
| 3 dB bandwidth (MHz) | 23.84 | n/a | 38.12 |
| Max. rejection bandwidth (MHz) | 42.56 | 40.00 | 56.24 |
| Shape Factor | 2.12 | n/a | 1.92 |

TABLE VI

COMPARATIVE DEVICE CHARACTERISTICS OF CIRCULAR SAW

| | Equivalent Circuit | FEM Sim. | Experimental |
|---|---|---|---|
| Center Frequency f$_0$ (MHz) | 325.50 | 321.8 | 323.16 |
| Insertion Loss at f$_0$ (MHz) | −3.13 | −25.19 | −27.23 |
| 3 dB bandwidth (MHz) | 35.11 | n/a | 44.20 |
| Max. rejection bandwidth (MHz) | 55.41 | 40.22 | 78.30 |
| Shape Factor | 2.44 | n/a | 2.43 |

What is claimed is:

1. An integrated circuit chip having a circular design SAW device as an on-chip component, the SAW device comprising one or more interdigital transducers formed in a substantially closed concentric circle arrangement.

2. The chip of claim 1, wherein the chip is a microprocessor.

3. The chip of claim 1, wherein the chip is a programmable integrated circuit.

4. The chip of claim 1, wherein the chip is a microelectromechanical system (MEMS).

5. The chip of claim 1, wherein the chip is a nanoelectromechanical system (NEMS).

6. The chip of claim 1, wherein the circular design SAW device is a CMOS device.

7. The chip of claim 6, wherein the circular design SAW device includes an absorber structure formed from stacked CMOS layers.

8. The chip of claim 7, wherein the CMOS layers are metal1, metal2, polysilicon and inter-layer oxides.

9. The chip of claim 1, wherein the concentric circular interdigital transducer structures are aligned on a common focal point.

10. The chip of claim 9, wherein the interdigital transducer structures are interconnected using CMOS layers.

11. The chip of claim 10, wherein the substantially closed concentric circle arrangement is a continuous completely closed concentric circle arrangement.

12. The chip of claim 1, wherein the substantially closed concentric circle arrangement is a continuous completely closed concentric circle arrangement.

13. A circular design SAW device having an absorber structure, the absorber structure formed from stacked CMOS layers of metal1, metal2, polysilicon and inter-layer oxides, wherein the SAW device comprises one or more interdigital transducers formed in a substantially closed concentric circle arrangement.

14. An LC circuit which comprises a circular design SAW device and an amplifier on the same chip, the SAW device comprising one or more interdigital transducers formed in a substantially closed concentric circle arrangement.

15. A local oscillator, which comprises the LC circuit of claim 14 connected to a Pierce oscillator.

* * * * *